United States Patent
Goldblum et al.

(10) Patent No.: US 11,771,702 B2
(45) Date of Patent: Oct. 3, 2023

(54) AGONISTS OF PPAR-δ

(71) Applicant: Amiram Goldblum, Tel Aviv (IL)

(72) Inventors: Amiram Goldblum, Tel Aviv (IL);
Jianwei Che, Sharon, MA (US);
Anwar Rayan, Kabul (IL); Binyamin Daadoosh, Tel Aviv Jaffa (IL); David Marcus, Cambridge (GB)

(73) Assignee: Amiram Goldblum, Tel Aviv (IL)

( * ) Notice: Subject to any disclaimer, the term of this patent is extended or adjusted under 35 U.S.C. 154(b) by 134 days.

(21) Appl. No.: 17/298,115

(22) PCT Filed: Nov. 28, 2019

(86) PCT No.: PCT/IL2019/051311
§ 371 (c)(1),
(2) Date: May 28, 2021

(87) PCT Pub. No.: WO2020/110126
PCT Pub. Date: Jun. 4, 2020

(65) Prior Publication Data
US 2022/0023308 A1    Jan. 27, 2022

Related U.S. Application Data

(60) Provisional application No. 62/773,660, filed on Nov. 30, 2018.

(51) Int. Cl.
*A61K 31/5377* (2006.01)
*A61K 31/165* (2006.01)
*A61K 31/192* (2006.01)
*A61K 31/195* (2006.01)
*A61K 31/341* (2006.01)
*A61K 31/40* (2006.01)
*A61K 31/415* (2006.01)
*A61K 31/42* (2006.01)
*A61K 31/426* (2006.01)
*A61K 31/4406* (2006.01)
*A61K 31/445* (2006.01)
*A61K 31/473* (2006.01)
*A61K 31/519* (2006.01)

(52) U.S. Cl.
CPC ........ *A61K 31/5377* (2013.01); *A61K 31/165* (2013.01); *A61K 31/192* (2013.01); *A61K 31/195* (2013.01); *A61K 31/341* (2013.01); *A61K 31/40* (2013.01); *A61K 31/415* (2013.01); *A61K 31/42* (2013.01); *A61K 31/426* (2013.01); *A61K 31/445* (2013.01); *A61K 31/4406* (2013.01); *A61K 31/473* (2013.01); *A61K 31/519* (2013.01)

(58) Field of Classification Search
CPC .............. A61K 31/5377; A61K 31/165; A61K 31/192; A61K 31/195; A61K 31/341; A61K 31/40; A61K 31/415; A61K 31/42; A61K 31/426; A61K 31/4406; A61K 31/445; A61K 31/473; A61K 31/519; A61P 3/06; A61P 3/10; A61P 35/00
See application file for complete search history.

(56) References Cited

PUBLICATIONS

ZINC, ZINC28073764. Added Sep. 23, 2009, available since Aug. 7, 2015. Retrieved from the internet on Dec. 21, 2022, https://zinc.docking.org/substances/ZINC000028073764/ (Year: 2009).*
ZINC, ZINC13015184. Added May 24, 2008, available since Aug. 7, 2015. Retrieved from the internet on Dec. 21, 2022, https://zinc.docking.org/substances/ZINC000013015184/. (Year: 2008).*
Da'Adoosh et al., "Discovering highly selective and diverse PPAR-delta agonists by ligand based machine learning and structural modeling", Scientific Reports, 2019, vol. 9, No. 1, 12 pages.
Fan et al., "PPAR-delta Promotes Running Endurance by Preserving Glucose", Cell Metab, 2017, vol. 25, No. 5, pp. 1186-1193.
Shearer et al., "Discovery of a novel class of PPAR delta partial agonists", Bioorg Med Chem Lett, 2008, vol. 18, No. 18, pp. 5018-5022.
Wu et al.., "Structural basis for specific ligation of the peroxisome proliferator-activated receptor delta", P Natl Acad Sci USA, 2017, vol. 114, No. 13, pp. E2563-E2570.

* cited by examiner

*Primary Examiner* — Brandon J Fetterolf
*Assistant Examiner* — Lauren Wells
(74) *Attorney, Agent, or Firm* — Vorys, Sater, Seymour and Pease LLP; Anthony P. Venturino

(57) ABSTRACT

Disclosed are PPAR receptor modulators and their uses in medicine. The novel agonists for PPAR-δ were found by screening molecules through a chemoinformatics-based model. The novel agonists for PPAR-δ are proposed for use in medicine.

19 Claims, 10 Drawing Sheets

AGONISTS OF PPAR-δ

TECHNOLOGICAL FIELD

This invention generally relates to PPAR receptor modulators and their uses in medicine.

BACKGROUND

Peroxisome Proliferator-Activated Receptors (PPARs) are a subgroup of the nuclear hormone receptor family. Its members, PPAR-α, PPAR-γ and PPAR-δ, are ligand-activated transcription factors. PPAR-α is expressed in muscle and heart tissues, but mainly in the liver. PPAR-γ acts as a master regulator of adipocyte formation. PPAR-δ is expressed in many tissues, but at low levels in the liver.

Like other transcription factors, PPARs form heteromers with retinoid X receptor (RXR) and additional co-activator proteins. By binding of PPARs to endogenous ligands such as fatty acids, eicosanoids, and oxysterols, these ligand-activated transcription factors function as fat sensors and maintain lipid and glucose homeostasis, which are important to prevent cancer, diabetes, obesity and atherosclerosis.

PPAR structures have two domains: the N-terminal is a DNA-binding domain, with a dual zinc-finger motif; and the C-terminal is a ligand-binding domain (LBD), which consists of 12 α-helices and 3 β-strands. These secondary elements form a large hydrophobic binding cavity of 1300 Å$^3$.

PPAR-δ may be a promising target and that is because its agonist has beneficial effects on obesity, insulin resistance, and reduces plasma glucose in rodent models of type 2 diabetes. In addition, studies on obese primates suggest this agonist decreases low-density lipoprotein (LDL), TG and insulin, and increases HDL. In sedentary human volunteers, this agonist prevented the decrease of HDL-c and apoA-1 levels by reducing the serum TGs [1]. It has been recently suggested that PPAR-δ promotes exercise endurance by preserving glucose [2].

There are, however, no current clinical studies of selective PPAR-δ agonists either as single targeted or multi-targeted, in combination with other protein receptors.

REFERENCES

[1] Shearer B G, et al. (2008) Discovery of a novel class of PPAR delta partial agonists. Bioorg Med Chem Lett 18(18):5018-5022.
[2] Fan W W, et al. (2017) PPAR delta Promotes Running Endurance by Preserving Glucose. *Cell Metab* 25(5): 1186-1193.
[3] Wu et al., (2017) Structural basis for specific ligation of the peroxisome proliferator-activated receptor delta. *P Natl Acad Sci USA* 114(13): E2563-E2570.

GENERAL DESCRIPTION

The present invention is based on the discovery of novel agonists for PPAR-δ that were found by screening a plentiful, commercially available, set of molecules through a cheminformatics-based model.

An ISE algorithm was used to create a highly efficient model, which distinguishes between known agonists and random molecules (presumed to be inactive molecules). The ISE algorithm is an iterative stochastic elimination algorithm which is a novel algorithm originally developed to solve extremely complex problems in protein structure and interactions, and has since been applied to diverse topics that share a few general "ingredients": they are extremely complex, of combinatorial nature, may be presented as large sets of variables that can each have many alternative values, there is some interdependence of the variables on each other, and there is a scoring function that can evaluate each choice of the problems "configuration"; this is the set of single values of each of the variables that constitute its full presentation. Those are picked randomly in a large sample, the analysis of which allows decisions to be made for rejecting some values for each of the variables; thus resulting in a smaller set of potential combinations. This continues in iterations until the number of combinations allows all remaining options to be computed exhaustively and to order them by their scores. ISE has been mainly applied to problems that are relevant to drug design and discovery. ISE can be used to determine the properties of molecular ensembles and to pick the best molecules ("focused libraries") for hitting a specific target.

ENAMINE database (an enumerated database of synthetically feasible molecules), composed of 1.56 million molecules, has been screened and scored by the ISE model, and top-scored molecules were docked to PPAR-δ. Molecules that showed potential activity by ISE scoring and by docking were used for in vitro testing. Out of 306 molecules tested, nearly 9% were found to have good to excellent binding affinities (List A): of which 13 molecules (List B) were found to have EC$_{50}$ in the nanomolar range (4 nM-19 nM) and 14 other molecules (List C) were found to have EC$_{50}$<10 μM (one of those with EC$_{50}$=883 nm). The top 14 active molecules (List C) with EC$_{50}$<1 μM are presented in Table 3, and the 13 additional molecules (List B) having EC$_{50}$>1 μM but below 10 μM are presented in Table 4. As known in the art, "EC$_{50}$" refers to the concentration of the 27 compounds described below or salts thereof, effective for half-maximal stimulation of PPAR-δ activity.

None of the 27 molecules (List A) discovered by screening had any previously known biological or medicinal properties. As such the use of these compounds as PPAR-δ agonists, affecting a variety of chronic diseases, disorders and conditions, is novel.

Therefore, according to one aspect, the invention provides a compound or a salt thereof, for use in medicine, wherein the compound is a compound of List A, selected from:

List A

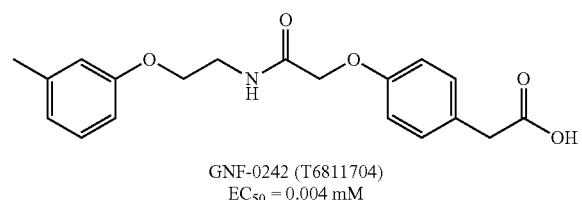

GNF-0242 (T6811704)
EC$_{50}$ = 0.004 mM

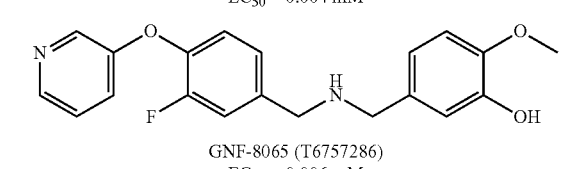

GNF-8065 (T6757286)
EC$_{50}$ = 0.006 mM

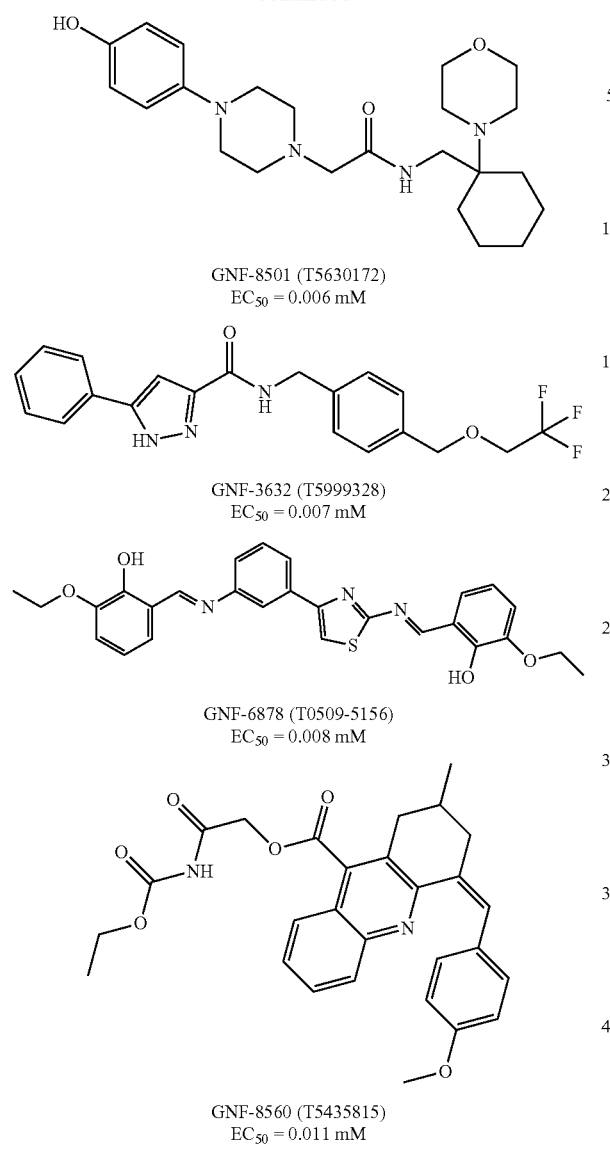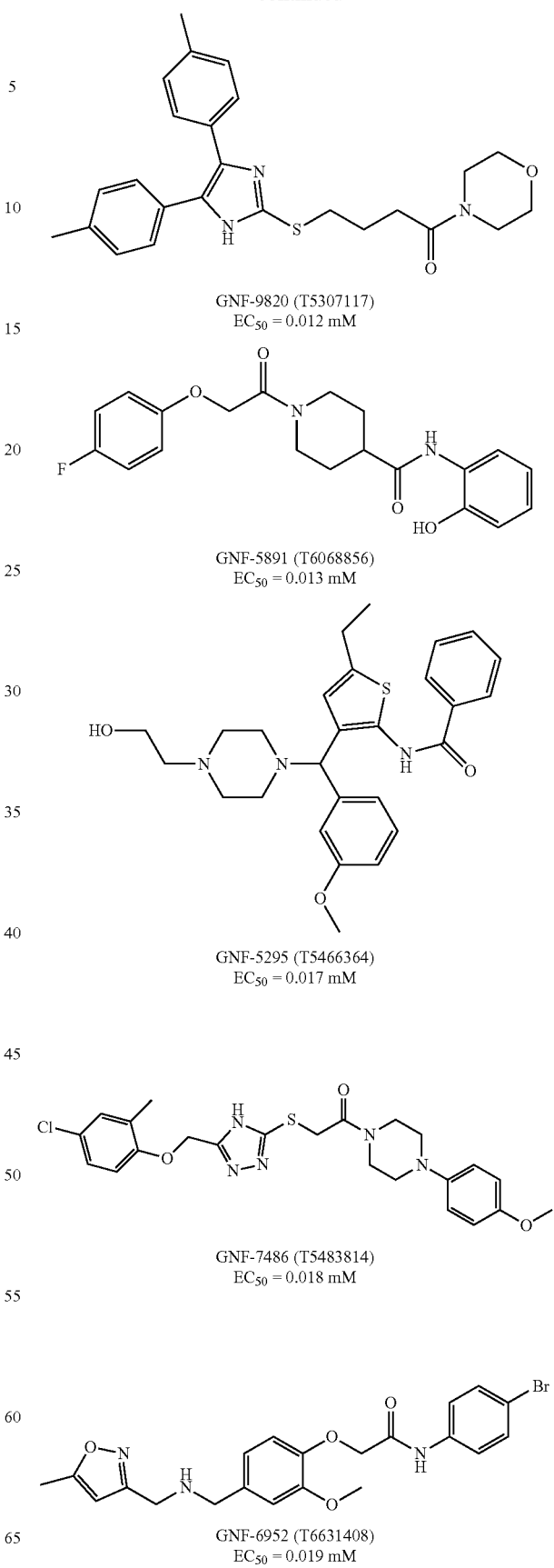

-continued
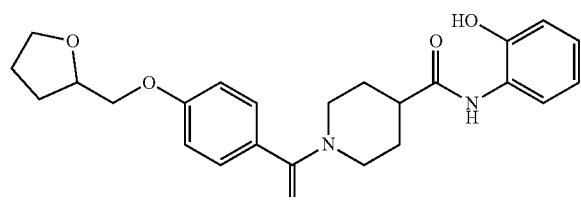
GNF-9448 (T5934377)
EC$_{50}$ = 0.883 mM
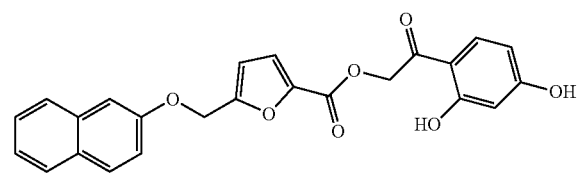
GNF-6928 (T6284002)
EC$_{50}$ = 3.698 mM
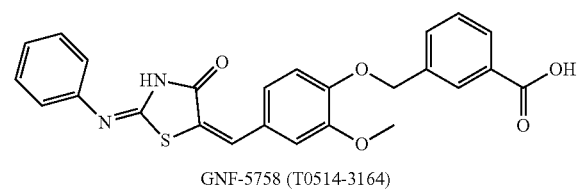
GNF-5758 (T0514-3164)
EC$_{50}$ = 4.327 mM
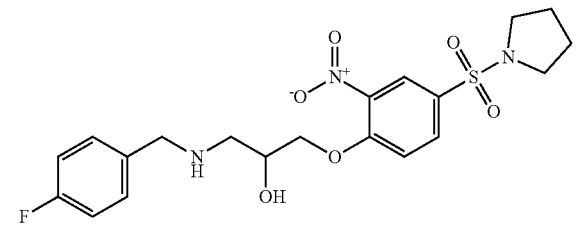
GNF-9594 (T5581560)
EC$_{50}$ = 4.598 mM
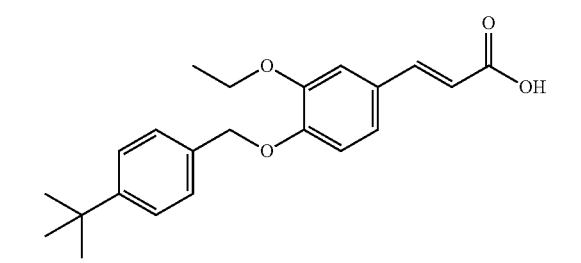
GNF-4516 (T0516-5980)
EC$_{50}$ = 6.815 mM
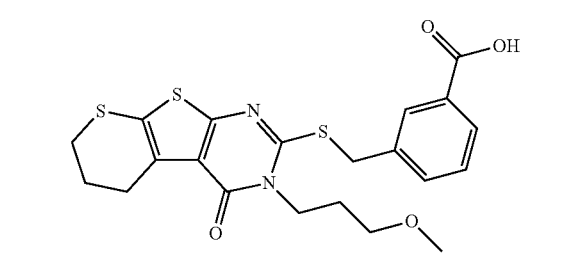
GNF-5154 (T6034605)
EC$_{50}$ = 7.045 mM
-continued
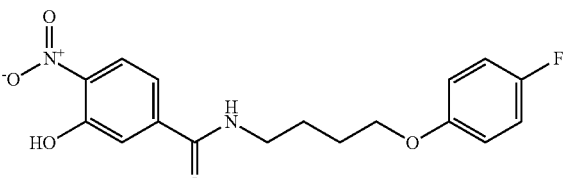
GNF-7176 (T5700057)
EC$_{50}$ = 7.239 mM
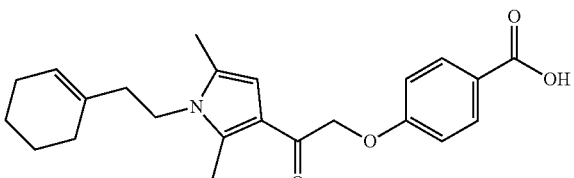
GNF-9057 (T5944667)
EC$_{50}$ = 7.488 mM
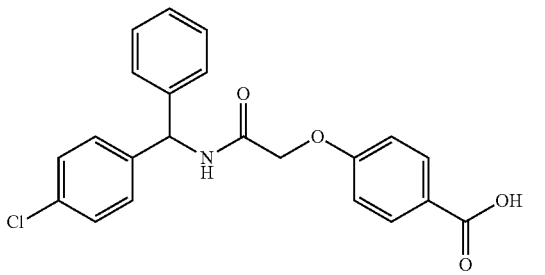
GNF-0248 (T5958543)
EC$_{50}$ = 7.555 mM
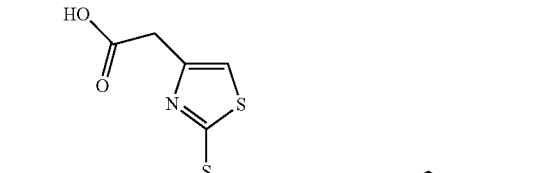
GNF-1051 (T5808401)
EC$_{50}$ = 7.757 mM
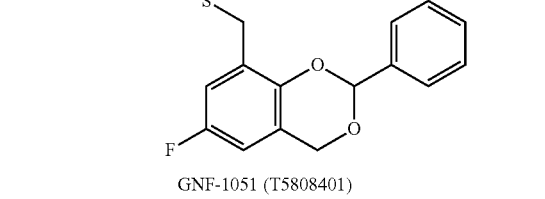
GNF-8208 (T6028636)
EC$_{50}$ = 7.858 mM
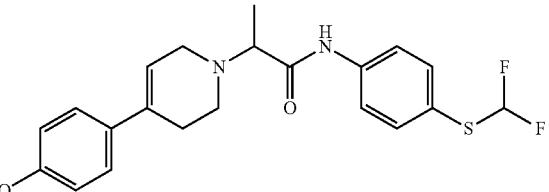
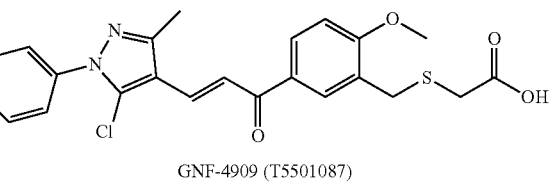
GNF-4909 (T5501087)
EC$_{50}$ = 8.239 mM -continued

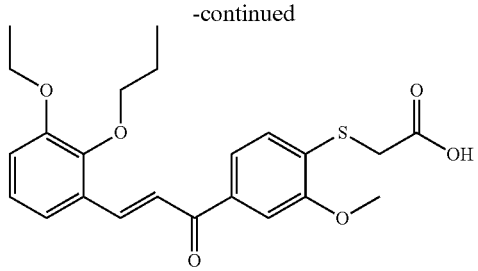

GNF-1676 (T6753746)
EC$_{50}$ = 8.387 mM

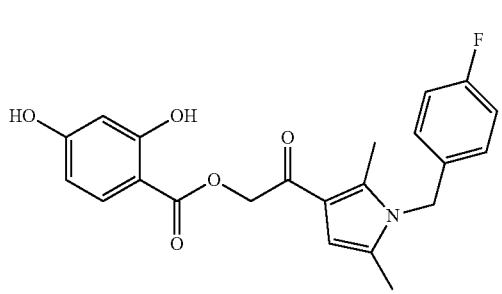

GNF-9969 (T6124323)
EC$_{50}$ = 9.481 mM

In some embodiments, the compound of List A is any one of GNF-0242 (T6811704) and/or GNF-8065 (T6757286) and/or GNF-8501 (T5630172) and/or GNF-3632 (T5999328) and/or GNF-6878 (T0509-5156) and/or GNF-8560 (T5435815) and/or GNF-0341 (T6163027) and/or GNF-6029 (T5894943) and/or GNF-9820 (T5307117) and/or GNF-5891 (T6068856) and/or GNF-5295 (T5466364) and/or GNF-7486 (T5483814) and/or GNF-6952 (T6631408) and/or GNF-9448 (T5934377) and/or GNF-6928 (T6284002) and/or GNF-5758 (T0514-3164) and/or GNF-9594 (T5581560) and/or GNF-4516 (T0516-5980) and/or GNF-5154 (T6034605) and/or GNF-7176 (T5700057) and/or GNF-9057 (T5944667) and/or GNF-0248 (T5958543) and/or GNF-1051 (T5808401) and/or GNF-8208 (T6028636) and/or GNF-4909 (T5501087) and/or GNF-1676 (T6753746) and/or GNF-9969 (T6124323), as designated herein.

In some embodiments, the compound is used in combination with one or more other active compound. In some embodiments, the compound is used as the only active compound.

In some embodiments, the compound is a salt of any of the compounds listed in List A. In some embodiments, the compound is two or more compounds listed in List A, or at least one other additional therapeutic agent, as disclosed herein.

In some embodiments, the compound of List A is selected amongst compound of List B or List C.

In some embodiments, the compound is a compound of List B:

List B

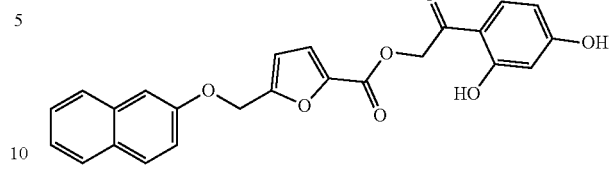

GNF-6928 (T6284002)
EC$_{50}$ = 3.698 mM

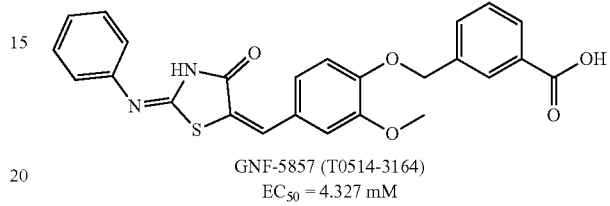

GNF-5857 (T0514-3164)
EC$_{50}$ = 4.327 mM

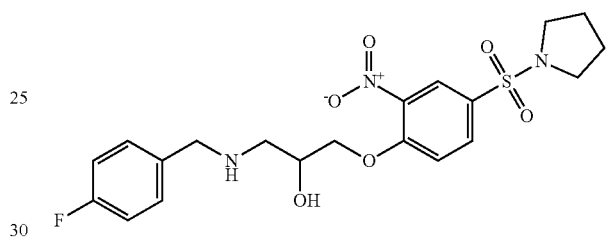

GNF-9594 (T5581560)
EC$_{50}$ = 4.598 mM

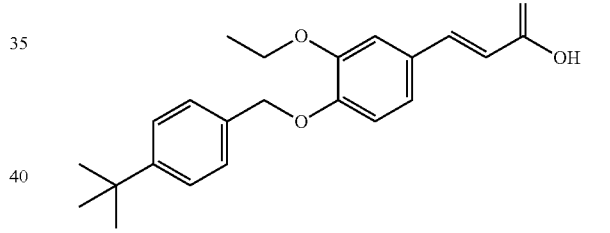

GNF-4516 (T0516-5980)
EC$_{50}$ = 4.598 mM

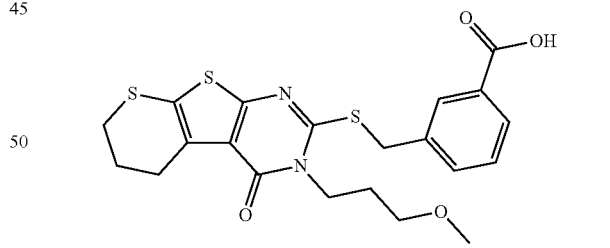

GNF-5154 (T6034605)
EC$_{50}$ = 7.045 mM

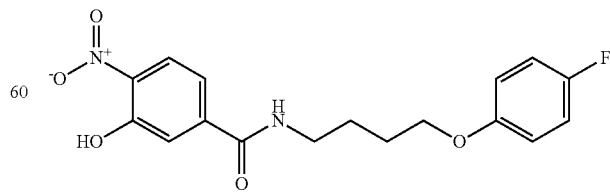

GNF-7176 (T5700057)
EC$_{50}$ = 7.239 mM

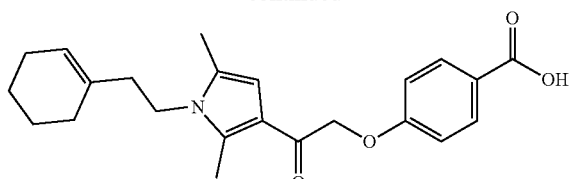
GNF-9057 (T5944667)
EC$_{50}$ = 7.488 mM
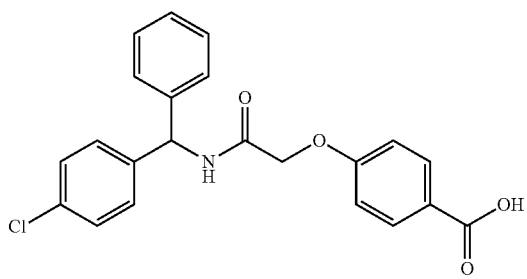
GNF-0248 (T5958543)
EC$_{50}$ = 7.555 mM
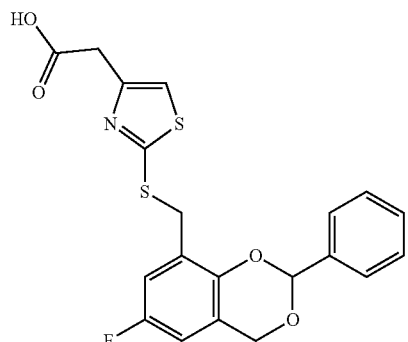
GNF-1051 (T5808401)
EC$_{50}$ = 7.757 mM
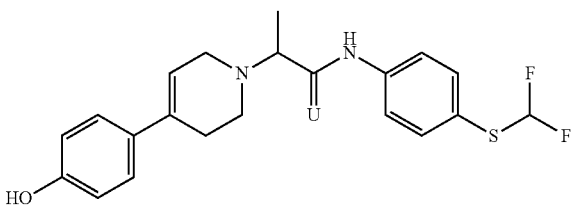
GNF-8208 (T6028636)
EC$_{50}$ = 7.858 mM
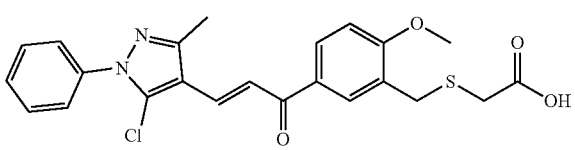
GNF-4909 (T5501087)
EC$_{50}$ = 8.239 mM
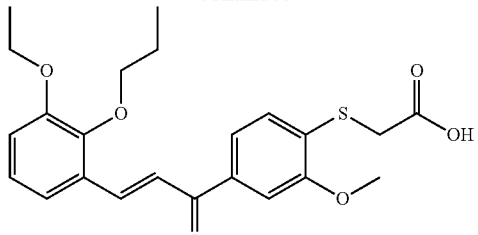
GNF-1676 (T6753746)
EC$_{50}$ = 8.387 mM
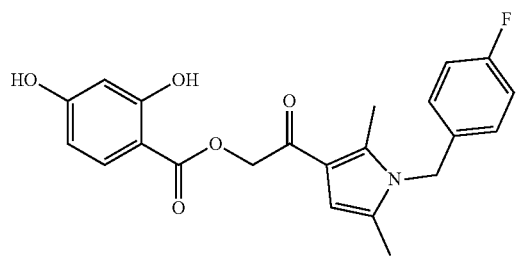
GNF-9969 (T6124323)
EC$_{50}$ = 9.481 mM
In some embodiments, the compound is a compound of List C:
List C
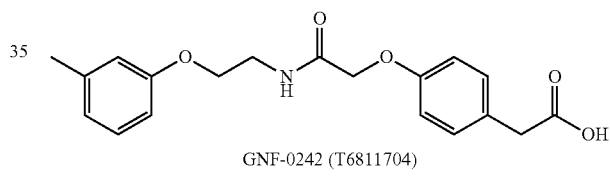
GNF-0242 (T6811704)
EC$_{50}$ = 0.004 mM
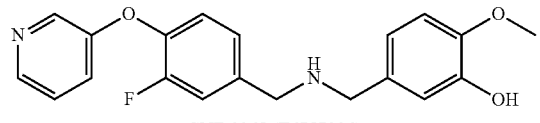
GNF-8065 (T6757286)
EC$_{50}$ = 0.006 mM
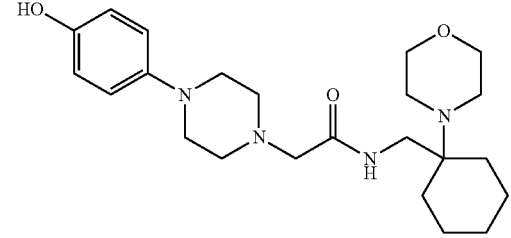
GNF-8501 (T5630172)
EC$_{50}$ = 0.006 mM
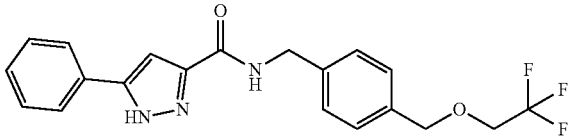
GNF-3632 (T5999328)
EC$_{50}$ = 0.007 mM

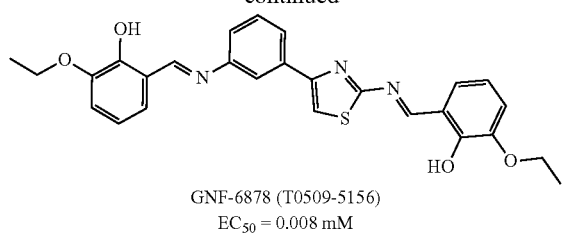
GNF-6878 (T0509-5156)
EC$_{50}$ = 0.008 mM
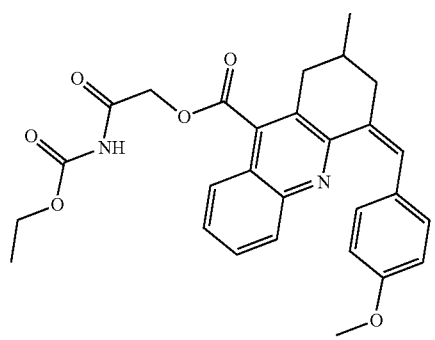
GNF-8560 (T5435815)
EC$_{50}$ = 0.011 mM
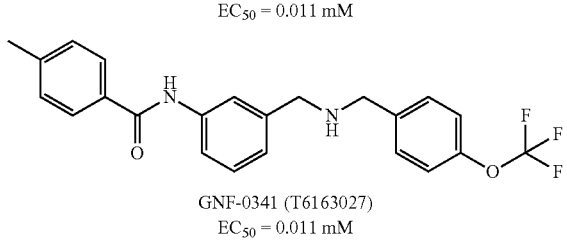
GNF-0341 (T6163027)
EC$_{50}$ = 0.011 mM
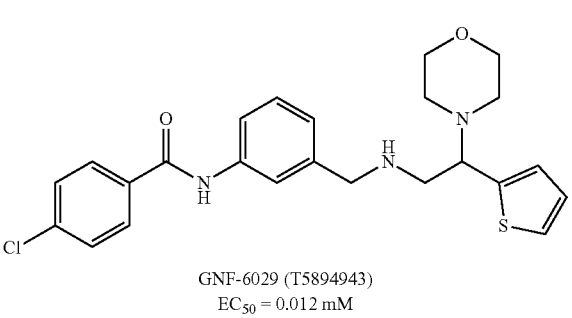
GNF-6029 (T5894943)
EC$_{50}$ = 0.012 mM
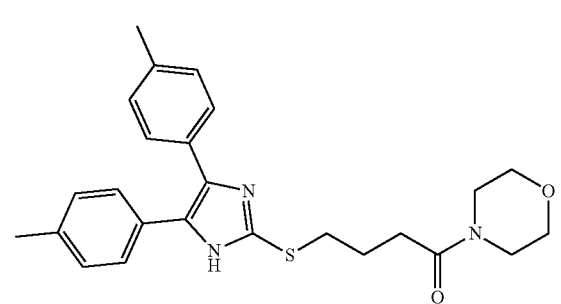
GNF-9820 (T5307117)
EC$_{50}$ = 0.012 mM
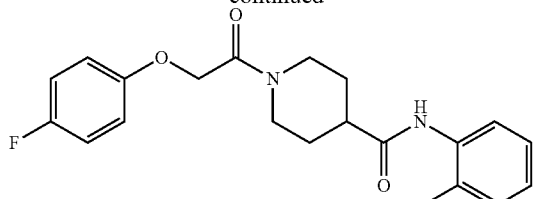
GNF-5891 (T6068856)
EC$_{50}$ = 0.013 mM
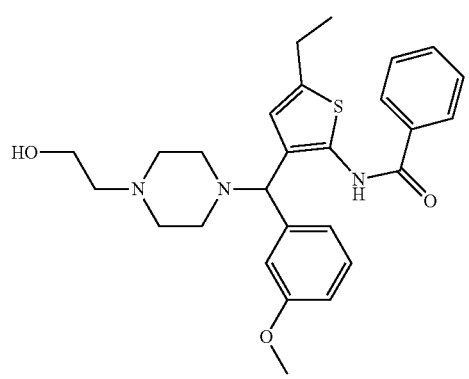
GNF-5295 (T5466364)
EC$_{50}$ = 0.017 mM
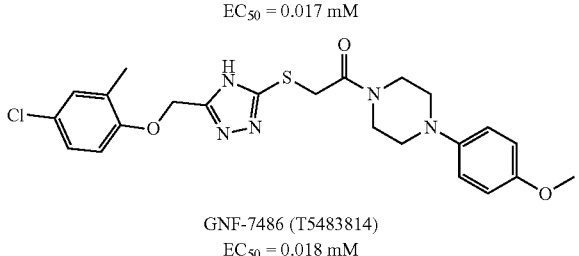
GNF-7486 (T5483814)
EC$_{50}$ = 0.018 mM
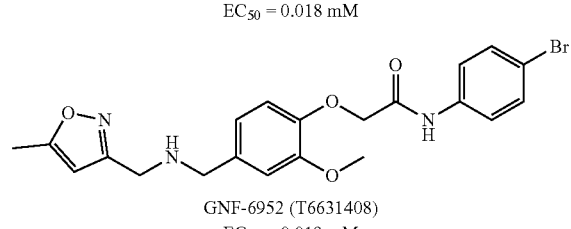
GNF-6952 (T6631408)
EC$_{50}$ = 0.019 mM
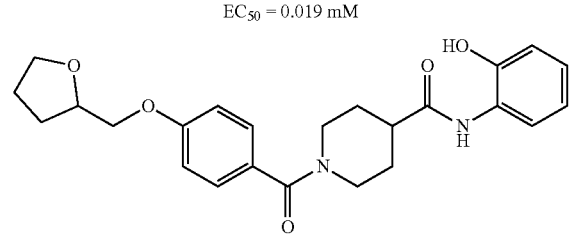
GNF-9448 (T5934377)
EC$_{50}$ = 0.883 mM
In some embodiments, the compound is any one of GNF-0242 (T6811704) and/or GNF-8065 (T6757286) and/or GNF-8501 (T5630172) and/or GNF-3632 (T5999328) and/or GNF-6878 (T0509-5156) and/or GNF-8560 (T5435815) and/or GNF-0341 (T6163027) and/or GNF-6029 (T5894943) and/or GNF-9820 (T5307117) and/or GNF-5891 (T6068856) and/or GNF-5295 (T5466364) and/or GNF-7486 (T5483814) and/or GNF-6952 (T6631408) and/or GNF-9448 (T5934377).

The compounds of List B and List C are contained in List A; thus, any recitation of "List A", unless otherwise specified, is interchangeable with "List B" or "List C".

Compounds used in accordance with the invention are commercially available. Synthesis of the compounds or chemical modifications thereof to yield salts, derivatives, isomers, stereoisomers, hydrates or any other pharmaceutically acceptable form, can be achieved using synthetic methodologies known in Organic Chemistry. Such methodologies are known to a person of skill in the art.

Pharmaceutically acceptable acid addition salts of compounds disclosed herein include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," J. of Pharmaceutical Science, 66:1-19 (1977)).

The acid addition salts of basic compounds may be prepared by contacting the free base form with a sufficient amount of a desired acid to produce the salt in the conventional manner. The free base form may be regenerated by contacting the salt form with a base and isolating the free base in the conventional manner Pharmaceutically acceptable base addition salts are formed with metals or amines, such as alkali and alkaline earth metals or organic amines Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," J. of Pharmaceutical Science, 66:1-19 (1977)).

The base addition salts of acidic compounds are prepared by contacting the free acid form with a sufficient amount of a desired base to produce the salt in the conventional manner. The free acid form may be regenerated by contacting the salt form with an acid and isolating the free acid in the conventional manner.

Thus, a "salt" form of any compound disclosed herein is a pharmaceutically acceptable salt which is suitable for use in contact with human or animal tissues without undue toxicity, allergic response or irritation. The salts may include without limitation those derived from suitable organic and non-organic acids and bases. Examples of such salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other meiliods used in the art such as ion exchange. Other pharmaceutically acceptable salts include adipate, alginate, ascorbate, aspartate, benzenesulfonate, benzoate, glucoheptonate, malonate, butyrate, camphorate, carnphorsulfonate, citrate, cyclopentanepropionate, digluconate, dodecylsulfate, ethanesulfonate, formate, fumarate, bisulfate, glycerophosphate, gluconate, hemisulfate, heptanoate, oxalate, hydroiodide, 2-hydroxy-ethanesulfonate, lactobionate, lactate, laurate, lauryl sulfate, malate, maleate, borate, methanesulfonate, 2-naphthalenesulfonate, nicotinate, nitrate, oleate, hexonate, pahnitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and alkyl ammonium salts of the form $N^+(C_{1-5}alkyl)_4$ salts.

Additional suitable salts may be any basic nitrogen-containing groups of molecules such as nontoxic ammonium, quaternary ammonium and amine cations formed using counter ions such as halide, hydroxide, carboxylate, sulfate, phosphate, nitrate, loweralkyl sulfonate and aryl sulfonate. Further pharmaceutically acceptable salts may include alkaline or alkali earth metal salts such as sodium, potassium, magnesium, lithium, calcium and the like.

Compounds used in accordance with the invention may additionally or alternatively be presented in a form of a derivative, an isomer, a stereoisomer, an enantiomer, a diastereomer, a hydrate or in any other pharmaceutically acceptable form. The compounds may also be in a semi-hydrate, an anhydrous, amorphous, crystalline or a polymorphous form.

For purposes known in the art, any one or more compound disclosed herein, alone or in combination, may be presented for administration in a from selected from a free acid form, a free base form, a salt form or a prodrug from (i.e., any derivative of a compound as used herein which upon administration dissociates or metabolizes to provide the compound in an active form, or to provide an active metabolite or a residue thereof).

The invention further provides a modulator of PPAR-δ, the modulator being a compound of List A. In some embodiments, the modulator is a compound of List B or List C.

The invention further provides a compound of List A for use as a modulator of PPAR-δ.

The "PPAR-δ", as used herein, refers to a peroxisome proliferator-activated receptor delta, also known as NR1C2 (nuclear receptor subfamily 1, group C, member 2), which is a nuclear hormone receptor that regulates a variety of processes. The nuclear hormone receptor may be involved in several chronic diseases, including, without limitation, obesity, type 2 diabetes, increased serum low-density lipoprotein (LDL), increased serum triglycerides (TG), decreased serum high-density lipoprotein (HDL), cancer, atherosclerosis, atherogenic dyslipidemia, non-alcoholic fatty liver disease, epidermis disorders, inflammation after gut ischemia/reperfusion injury and lung inflammation.

Compounds used in accordance with the invention acting as modulators of the PPAR-δ, may be regarded as receptor antagonists, receptor agonists, receptor partial agonists, allosteric modulators and inverse agonists. In some embodiments, compounds of List A act as receptor agonists. The term "agonist", as used herein, refers to the ability of the compounds to bind the receptor, in any way, and to activate the receptor to evoke a biological action. As known, PPAR-δ can induce an effect on different types of cells and tissues and its mechanism is connected to many types of diseases and disorders. Non-limiting list of the diseases and disorders may include obesity, type-2 diabetes, increased serum low-density lipoprotein (LDL), increased serum triglycerides (TG), decreased serum high-density lipoprotein (HDL), cancer, atherosclerosis, atherogenic dyslipidemia, non-alcoholic fatty liver disease, epidermis disorders, inflammation after gut ischemia/reperfusion injury and lung inflammation. Also, PPAR-δ promotes exercise endurance by preserving glucose.

Thus, compounds of List A or salts thereof, independently or in a combination, may be used for treating or preventing obesity, type 2 diabetes, increased serum low-density lipoprotein (LDL), increased serum triglycerides (TG), decreased serum high-density lipoprotein (HDL), cancer, atherosclerosis, atherogenic dyslipidemia, non-alcoholic fatty liver disease, epidermis disorders, inflammation after gut ischemia/reperfusion injury or lung inflammation.

Compounds used in accordance with the invention (List A, List B, List C) may be used to maintain therapeutically acceptable serum levels of LDL, HDL and TG. As such, these compounds are useful in maintaining low levels of LDL, by preventing an increase in LDL serum levels; in maintaining high levels of HDL, by preventing a decrease in HDL serum levels; and by preventing an increase in TG levels.

As used herein, the term "cancer" is a medical term used to describe a severe and progressively worsening disease which potentially poses a mortal threat to the suffering subject. As known in the art, there is a wide spectrum of cancers, such as blastoma, carcinoma, lymphoma, leukemia, sarcoma, mesothelioma, glioma, germinoma, choriocarcinoma, melanoma, glioblastoma, lymphoid malignancies, squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer, breast cancer, prostate cancer, sarcomas, and skin cancer (such as melanoma).

"Non-alcoholic fatty liver disease" refers to a medical state wherein a subject suffers from a fatty liver without having a history of alcohol consumption or abuse and in cases where alcohol consumption is not related to the occurrence. Fatty liver is caused by a lipid metabolism disorder or a defect in the process of carrying excessive fat in the liver cells, and is mainly caused by disorders of lipid metabolism in the liver. The fatty liver of subjects suffering from the disease is characterized by an abnormal accumulation of triglyceride in liver cells. If the amount of triglycerides is more than 5% of the liver weight, the liver is classified as a fatty liver. The non-alcoholic fatty liver disease includes manifestations such as NAFLD, NASH, cirrhosis and HCC.

It is also known that management of energy stores is vital during endurance exercise; a shift in the utilization of glucose toward fat is a sign of trained muscle. This key metabolic adaptation is dependent on muscle PPAR-δ which is activated by PPAR-δ ligand. Furthermore, it has been found that muscle PPAR-δ expression positively correlates with endurance performance in BXD mouse reference populations. In addition to stimulating fatty acid metabolism, PPAR-δ activation potently suppresses glucose catabolism. By preserving glucose levels, PPAR-δ delays the onset of hypoglycemia and also extends the running time. Therefore, in some embodiments, the compound is for promoting exercise endurance.

In another one of its aspects, each one of the compounds of List A, or salts thereof, independently or in a combination may be used for preparing a composition or a formulation suitable for use in medicine. In some embodiments, the composition is a pharmaceutical composition.

Also provided is a pharmaceutical composition comprising an effective amount of a compound of List A, List B or List C, and optionally at least one carrier. As used herein, the "pharmaceutical composition" comprises a therapeutically effective amount of a compound disclosed herein, optionally together with suitable additives such as diluents, preservatives, solubilizers, emulsifiers, adjuvant and/or carriers. The compositions may be liquids or lyophilized or otherwise dried formulations and include diluents of various buffer content (e.g.; Tris-HCL, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), and others.

In some embodiments, the composition may further comprise one or more additional therapeutic agents, e.g., such as those commonly used in the treatment or prevention of a diseases or disorder disclosed herein or in the amelioration of one or more symptom associated therewith.

Compositions suitable for oral administration can comprise of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions or self-emulsifying formulations. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Compositions suitable for parenteral administration include sterile nanoemulsions, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives.

Compounds used in accordance with the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid.

Compounds used in accordance with the present invention may be made into injectable formulations. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).

Compounds used in accordance with the invention may be administered by various routes. Examples of such routes, without limitation may be sublingual, intranasal, oral administration, transdermal delivery, intradermal delivery, subcutaneous delivery, intramuscular, intravenous, intrathecal, rectal, vaginal, intraocular, transdermal, respiratory mucosal and other pulmonary routes of administration.

According to the invention, an "effective amount" of a compound of any of List A, B or C is an amount effective for achieving treatment or prevention, as disclosed herein, of any of the aforementioned diseases or disorders.

In some embodiments, the composition is for use in preventing or treating obesity, type 2 diabetes, increased serum low-density lipoprotein (LDL), increased serum triglycerides (TG), decreased serum high-density lipoprotein (HDL), cancer, atherosclerosis, atherogenic dyslipidemia, non-alcoholic fatty liver disease, epidermis disorders, inflammation after gut ischemia/reperfusion injury or lung inflammation.

In yet another aspect, each compound or salt thereof, as listed in List A, independently or in combination, may be used in a method of treatment of a subject (human or non-human) In some embodiments, the use is for preventing or treating any of the diseases and disorders disclosed herein.

Another aspect provides a method of treating or preventing a disease or disorder in a subject, the method comprising administering at least one compound of List A or a salt thereof to the subject. In some embodiments, the compound is contained in a pharmaceutical composition.

The term "treatment or prevention", or any lingual variation thereof, as used herein refers to the administering of a therapeutic amount of the at least one compound of List A or a composition containing same which is effective to ameliorate undesired symptoms associated with a disease or disorder as disclosed herein, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

Another aspect of the invention relates to a method of modulating PPAR-δ activity in vivo or in vitro (i.e., in a subject of in a biological sample), which method comprises contacting a cell or a tissue at least one compound of List A or a salt thereof or with a composition comprising same, wherein the cell or tissue is a cell or tissue of a subject or of a biological sample. In some embodiments, the method is carried out on a subject and thus the cell or tissue may be any cell or tissue which PPAR-δ activity is modulated. In some embodiments, the method is a diagnostic method carried out in vitro on a sample, e.g., a biological sample, obtained from a subject.

Also provided is a use of any one compound of List A or a salt thereof, for modulating the activity of PPAR-δ.

The term "biological sample", as used herein, includes, without limitation, cell cultures or extracts thereof; biopsied material obtained from a mammal or extracts thereof; feces, saliva, urine, blood, tears, semen, or other body fluids or extracts thereof. Modulation of nuclear receptor activity in general and PPAR-δ activity in particular, in a biological sample, is useful for a variety of purposes. Examples of such purposes may include, without limitation, a comparative evaluation of new modulators of PPAR-δ; the study of PPAR-δ in biological, physiological and pathological phenomena; and the study of new drugs, compounds or compositions related to the activity of PPAR-δ.

As the measurement of the activity of PPAR-δ or a fragment thereof may be useful for a variety of purposes such as study of new drugs or compounds related thereto; and the study of the roles of PPAR-δ in biological, physiological and pathological processes, in another one of its aspects, the invention provides a kit for use in measuring the activity of PPAR-δ or a fragment thereof in a biological sample in vivo or in vitro, wherein the kit comprising:

at least one compound of List A or a salt thereof and at least one pharmaceutically acceptable carrier, wherein the at least one compound of List A or a salt thereof and the at least one pharmaceutically acceptable carrier are separately presented or combined; and instructions for use.

In some embodiments, the kit comprises at least one vial or container, one or more of said at least one vial or container comprises the at least one compound of List A and another of said at least one vial or container comprises a reconstitution medium or a carrier for formulating a pharmaceutical composition for in vivo or in vitro use.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 6A shows an enrichment plot. FIG. 6B shows an enrichment plot of the highest indexed 1% of chemicals.

FIG. 7A depicts a receiver operating characteristic (ROC) curve. FIG. 7B depicts a ROC curve of the highest indexed 1% chemicals.

FIG. 8A shows a comparison vs. the novel agonists in this paper. FIG. 8B shows comparison of these novel agonists among themselves.

FIG. 9A presents a comparison of the 789 known agonist set vs. novel agonists. FIG. 9B presents a comparison of novel agonists among themselves. FIG. 9C presents a comparison is between the discovered 27 agonists and the randomly picked set of 5000.

DETAILED DESCRIPTION OF EMBODIMENTS

Methods

Figure 1B:
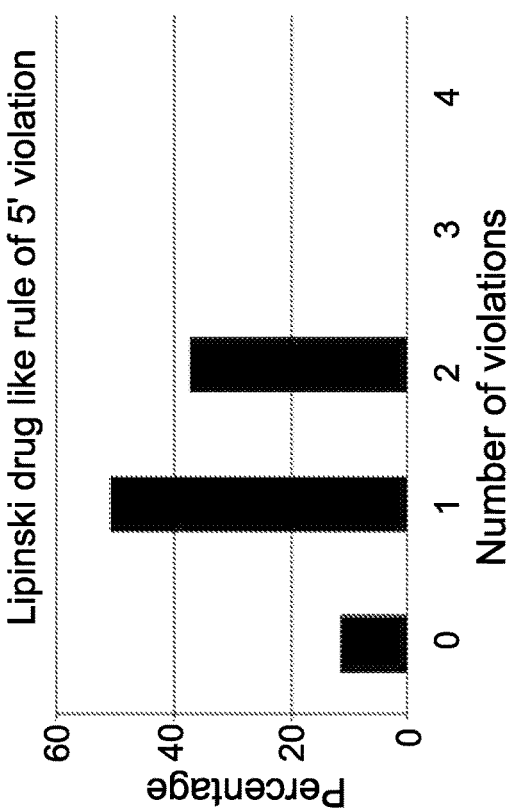
FIGS. 1A-D depict distribution plots of the Lipinski drug-like rule of 5 (ROF) violations (FIGS. 1A-B) and Oprea lead-like rules' violations for the set of PPAR-δ ligands (FIGS. 1C-D).
Figure 1D:
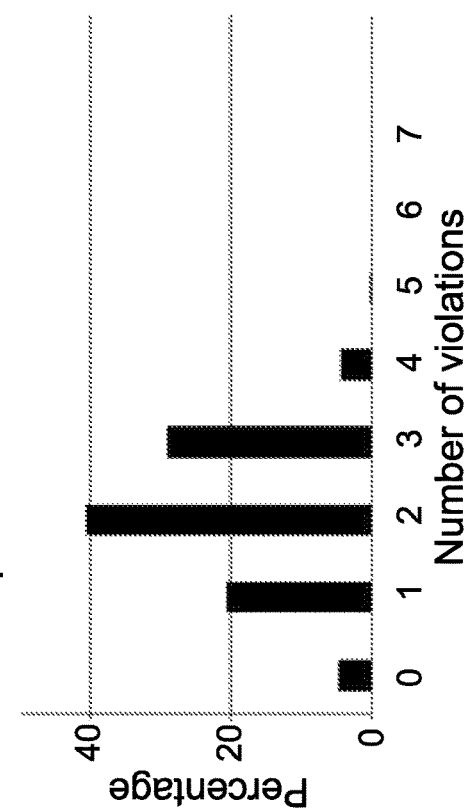
Figure 1A:
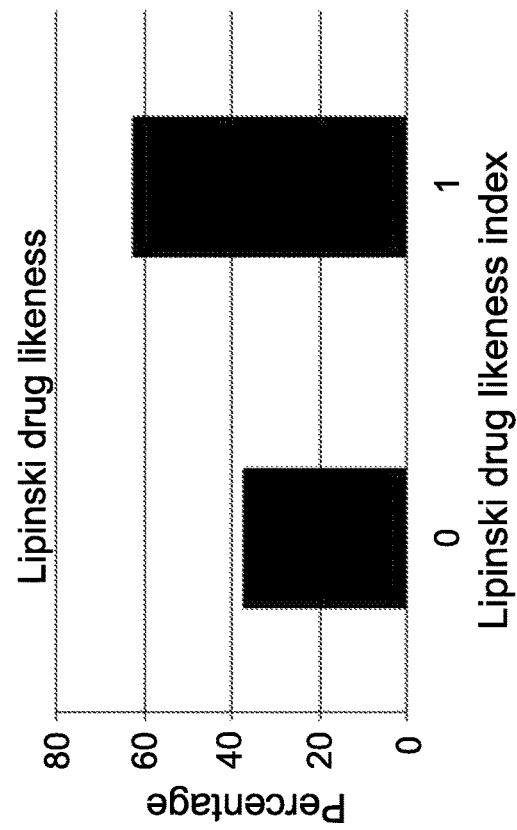
Figure 1C:
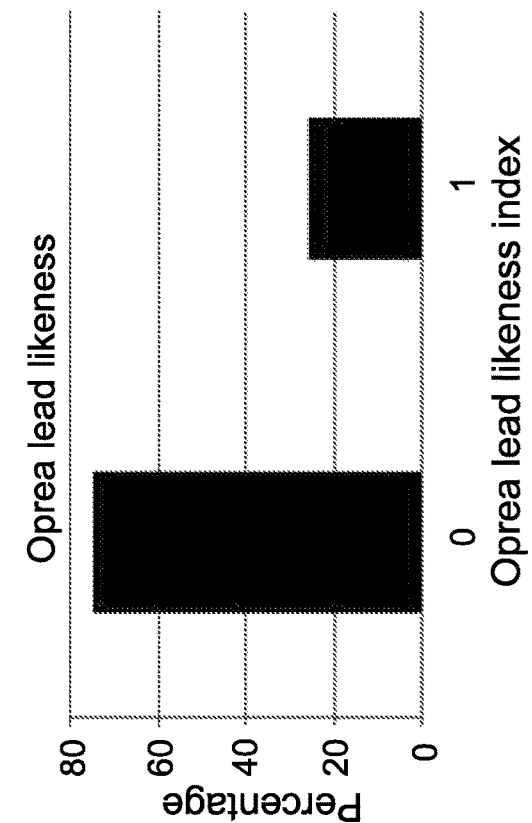
Figure 2A:
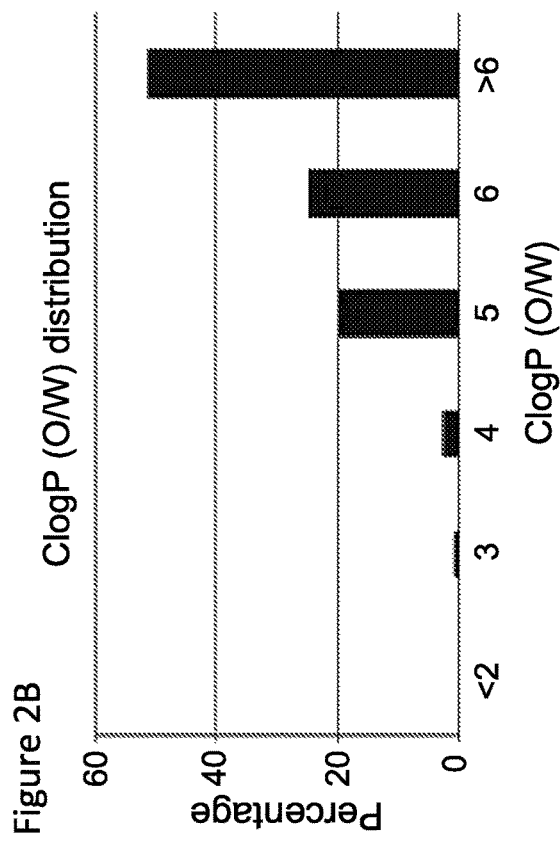
FIGS. 2A-D depict distribution plots of the four "Rule of 5" descriptors of Lipinski for the set of PPAR-δ agonists.
Figure 2B:
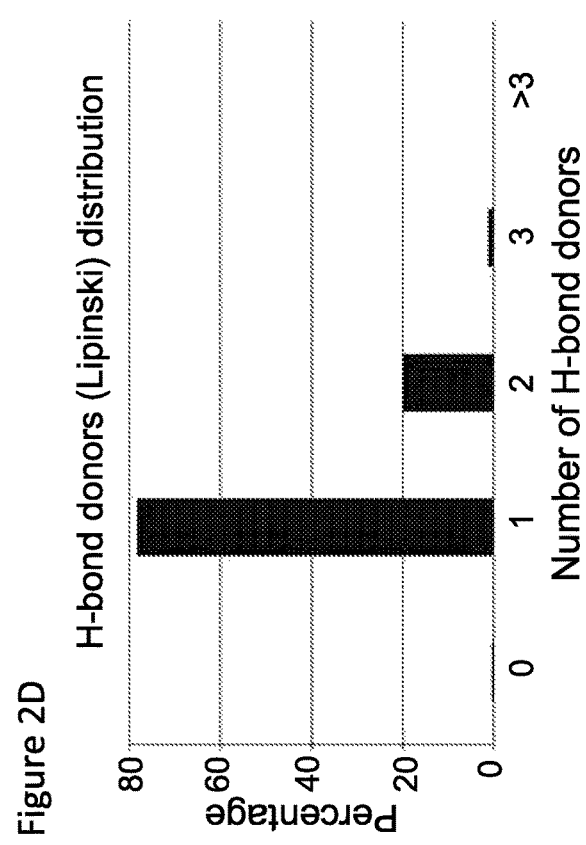
Figure 2C:
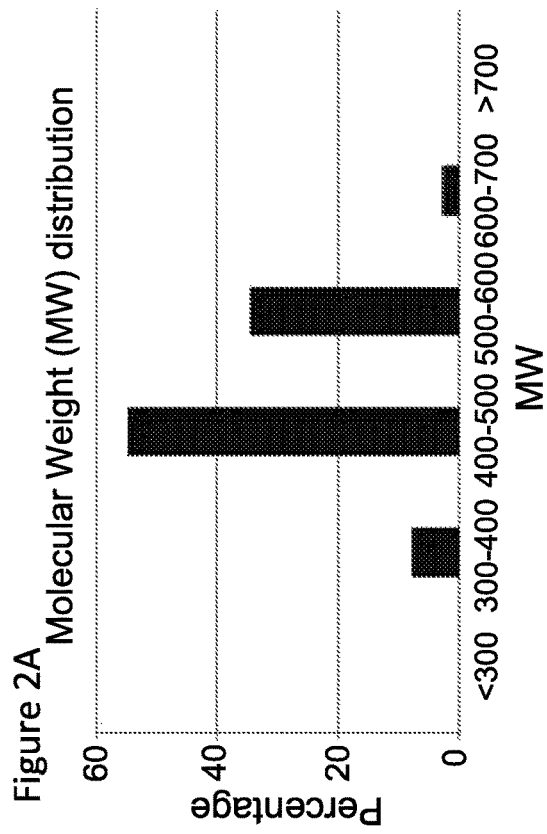
Figure 2D:
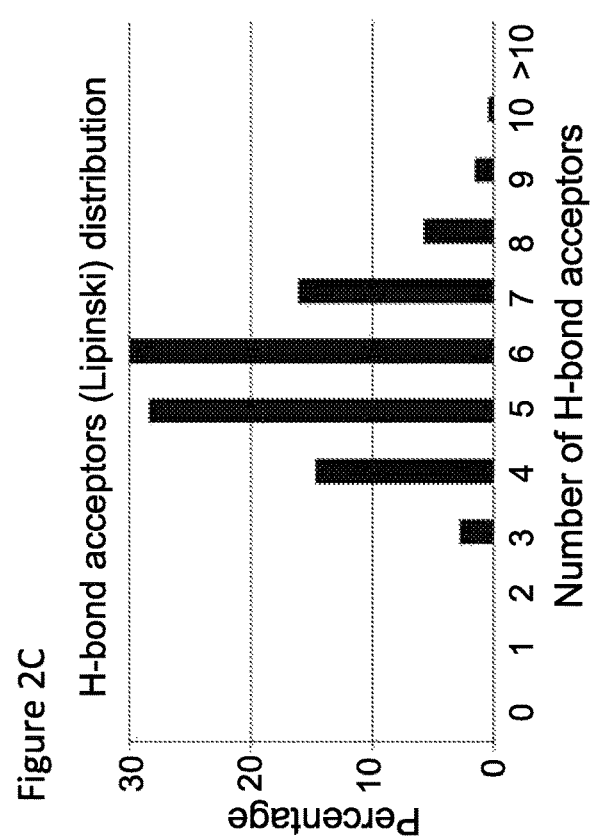

The calculations of physico-chemical (descriptors) values, of ranges of applicability domain, of the docking (including an analysis of data from the PDB and the results of OpenEye (Version 3.0), and the experimental in vitro measurements of agonist activities Tanimoto comparisons between the various sets and among molecules from the same set were made by OpenBabel (Version 2.1.1) (FP2 fingerprint). For general information on the building of an ISE model see FIG. 1.

Calculating values of Physico-chemical properties (descriptors) —values of Physico-chemical properties were calculated by MOE2010 for each molecule in each set (actives, inactives and ENAMINE database). These values were used to validate if the molecules obey the Rule of 5 and the Oprea rule, as well as to calculate the ranges of the applicability domain, and are the basis for producing the ISE model. In the case of Wu et al [3] agonists, the calculations of properties were performed by MOE2011.

Calculating ranges of applicability domains—the requirement that randoms should bear some main similarities to the active molecules was applied: applicability domain according to Lipinski's "rule of 5" properties (values depend on the set of actives) was used: Numbers of H-bond acceptors and H-bond donors, calculated log P and Molecular Weight. Properties were calculated by MOE software (by the descriptors: lip_acc (all N+O), lip_don (all OH+NH), log P(o/w) and molecular weight) for the known agonists and the random molecules. Mean values and standard deviations of the inhibitors were calculated for each of the properties, and a range of −2σ to 2σ was applied in order to include randomly picked molecules.

Collecting information from the PDB complexes—we summarized these interactions of each complex by using the LigPlot program (data was collected from the complex entries of PDBsum, on the "Ligand" tab). We used default distances, as we mentioned above. Ramachandran Plots were produced by PROCHECK.

Preparation of the PDB complexes and the small molecules, rigid docking and geometrical analysis—for each selected complex of PPAR-δ, some additional preparations in Sybyl-X 2.0 were required. First, we removed all the water molecules. Second, hydrogens were added to the whole protein. Third, we minimized the added hydrogens only. The Force Field was Tripos, the Charge was Gasteiger-Hückel, and the Dielectric Constant used was 4. The minimization was performed in two steps: first, Steepest descent followed by conjugate gradient with 10,000 steps to termination when the difference between successive minimization steps was <0.001 kcal/(mol*Å). A grid for docking was constructed by the MAKE RECEPTOR 3.0.0 (OpenEye) using default parameters.

In preparation for docking, 200 conformations were created for each molecule by the Omega program (OpenEye). Rigid docking of each was performed by Fred (OpenEye) using default parameters. For each molecule, 30 ligand poses with best energy scores were picked for analysis. For each pose, distances to the chosen residues were measured, as we mentioned above. A molecule was considered "successfully docked" if at least one of its poses fulfilled the geometrical conditions.

Measuring molecular agonist activities—a GAL4-DNA Binding Domain (GAL4-DBD) fusion protein was constructed for each PPAR family member. To assess compound activity, each construct was co-transfected into HEK293T cells (American Type Culture Collection; Manassas, Va.) along with the reporter construct, pGL5 (Promega) using Fugene 6 (Promega) as a transfection reagent and the manufacturer's protocol. An eleven-point dilution series of each compound was added to the cells and incubated overnight. Luciferase levels were then determined following the addition of Bright-Glo (Promega) using the manufacturer's recommendations. EC50 values were fitted to sigmoidal curves using four-parameter logistic regression (GraphPad). hPPARα/LBD encoding amino acids 175-468 (Genbank accession #NM_001001928), hPPARδ/LBD encoding amino acids 147-441 (Genbank accession #NM_006238) and hPPARγ/LBD encoding amino acids 184-477 (Genbank accession #NM_138712).

Each of the 306 candidates that were selected was tested as an agonist of PPAR-α, PPAR-γ, and PPAR-δ.

FIG. 1 depicts distribution plots of the Lipinski drug-like rule of 5 (ROF) violations and Oprea lead-like rules' violations for the set of PPAR-δ ligands: Upper left row, left: Lipinski drug-likeness 0=agonists that do not obey, 1=agonists obeying the rule), upper row, right: Distribution of ROF violations—37% of known agonists violate 2 or more of the 4 rules. Lower row, left: Oprea lead-likeness rules, 0=agonists that do not obey the rules, 1=25% which obey. Lower row left: Distribution of number of violations of Oprea lead-like rules.

FIG. 2 depicts distribution plots of the four "Rule of 5" descriptors of Lipinski for the set of PPAR-δ agonists. Upper left and clockwise: percentages of Molecular weights, of C Log P values, of the numbers of H-bond donors, and the numbers of H-bond acceptors.

Figure 3A:
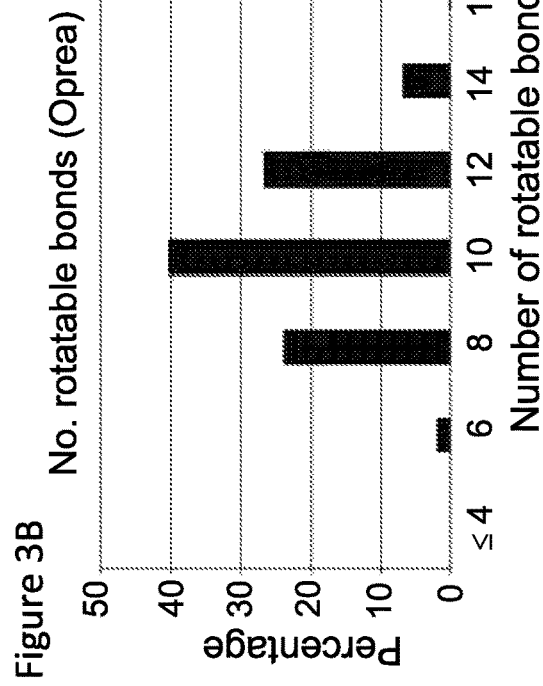
FIGS. 3A-C depict distribution plots of three additional lead-likeness descriptors of Oprea for the set of PPAR-δ agonists.
Figure 3B:
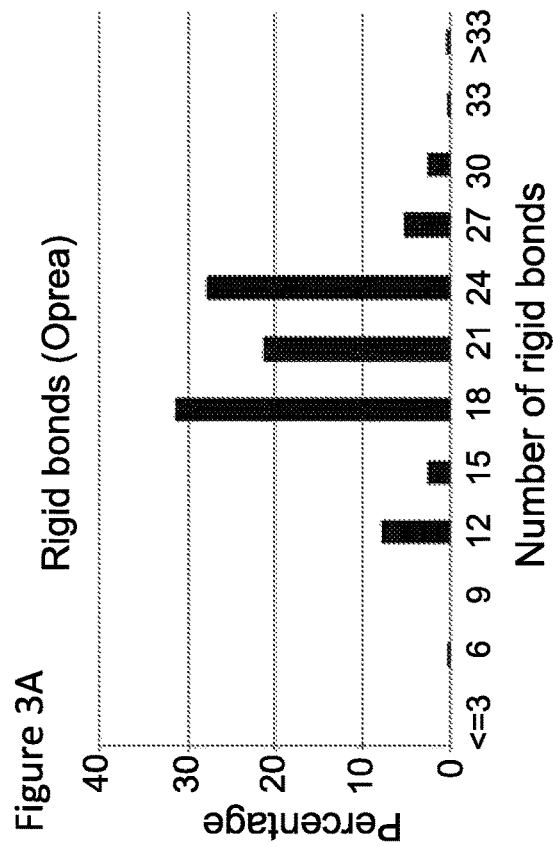
Figure 3C:
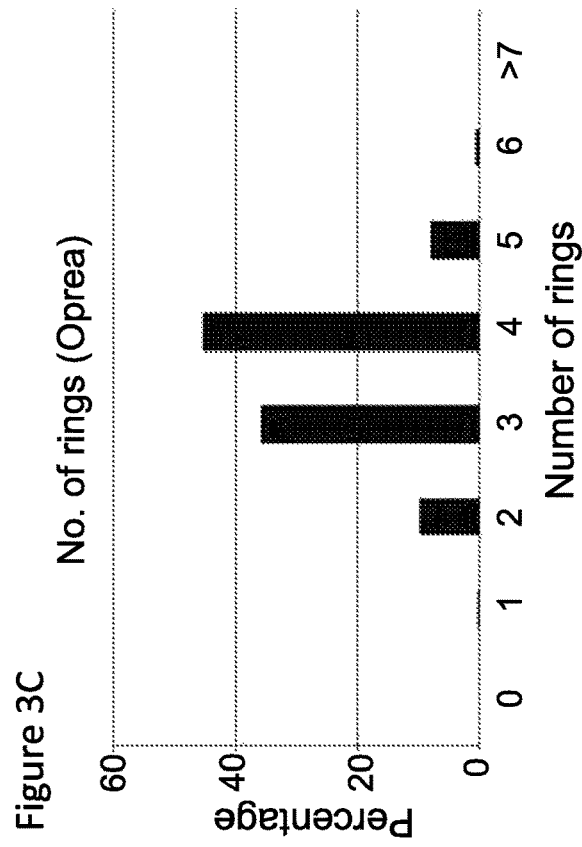

FIG. 3 depicts distribution plots of three additional lead-likeness descriptors of Oprea for the set of PPAR-δ agonists: Numbers of rigid bonds, Number of rotatable bonds, Numbers of rings.

Figure 4:
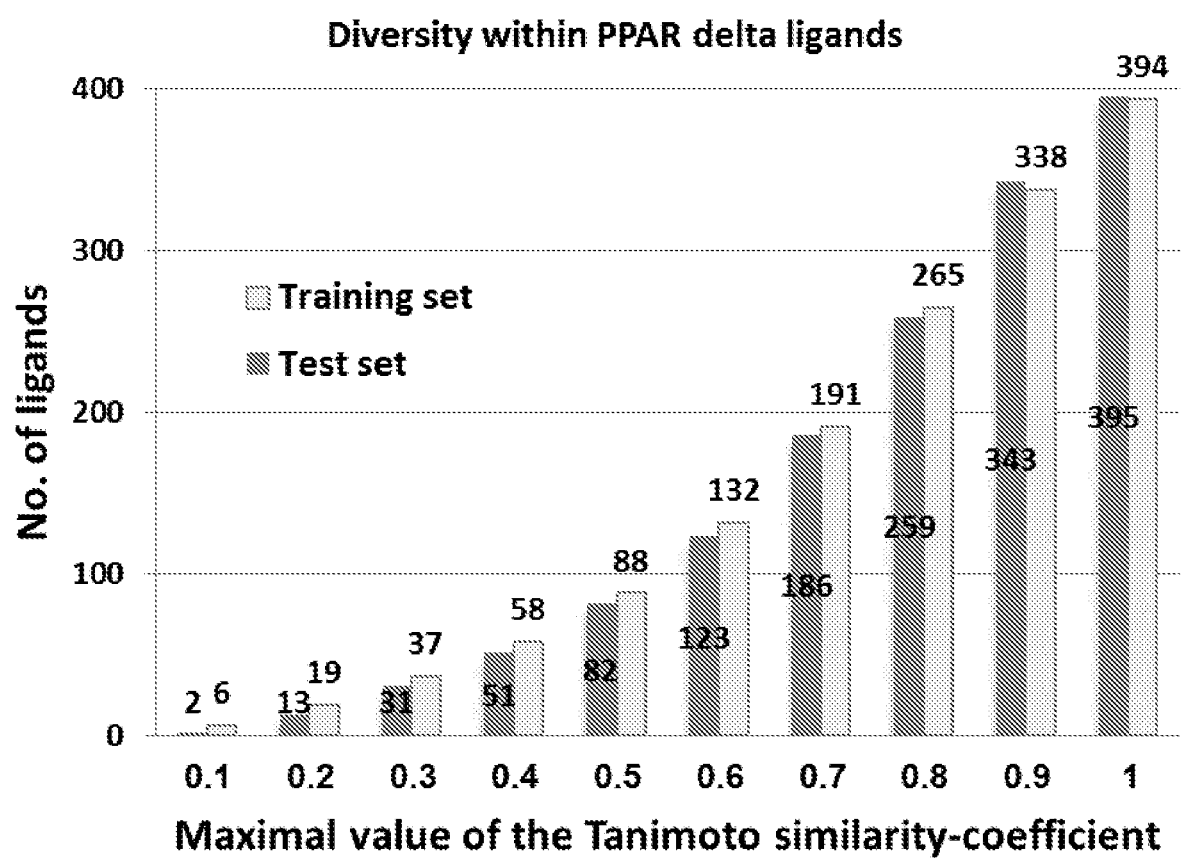
FIG. 4 depicts diversity within the training and test sets of PPAR-δ agonists that were used for modeling.

FIG. 4 depicts diversity within the training and test sets of PPAR-δ agonists that were used for modeling. The number in each bar indicates the active molecules that have remained at each "cutting level" of Tanimoto similarity.

Figure 5:
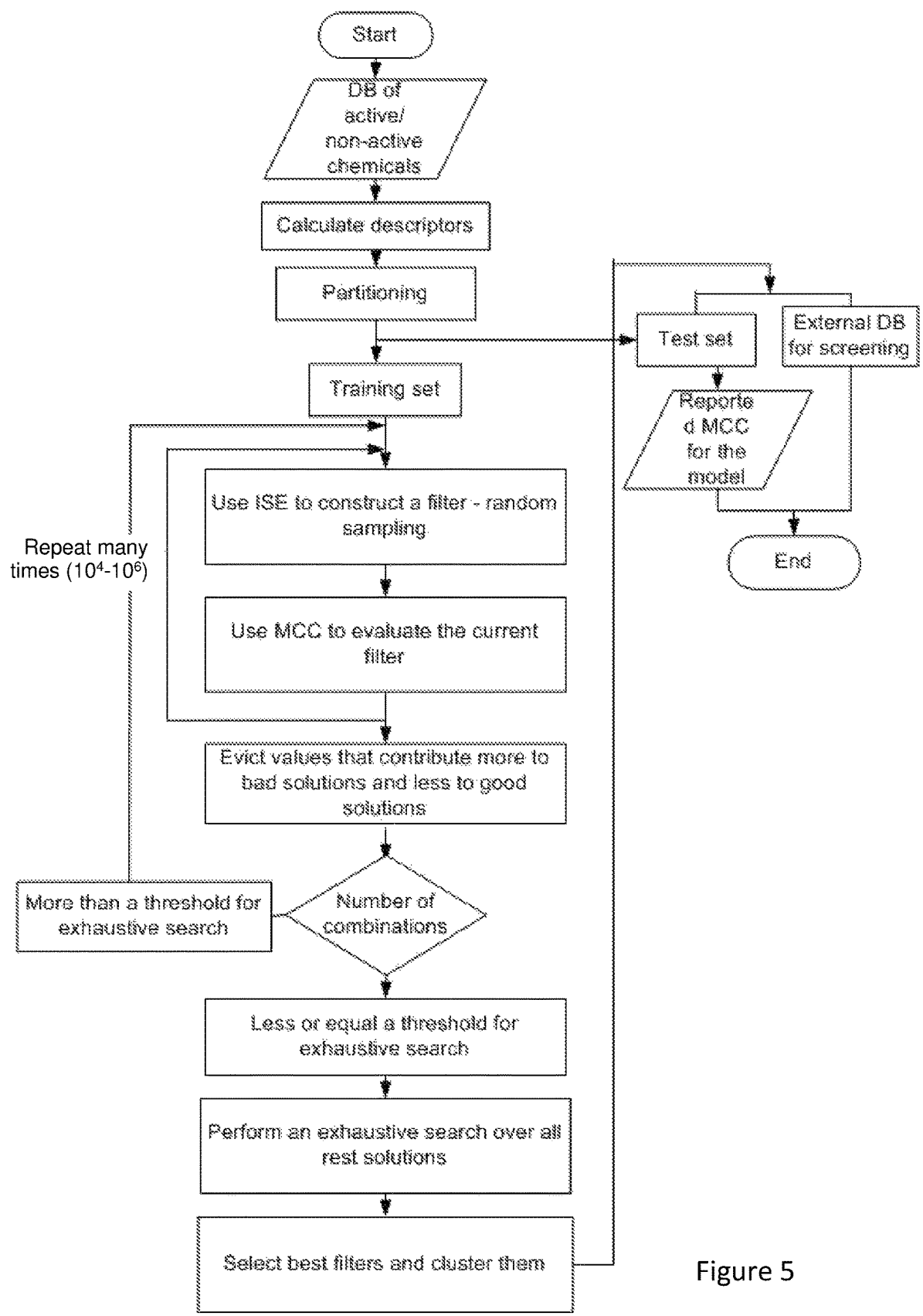
FIG. 5 presents a flowchart of the ISE algorithm.

FIG. 5 presents a flowchart of the ISE algorithm.

TABLE 1

The most redundant descriptors in the 68 filters, i.e., those that appear more than others among the 272 descriptor ranges (68 filters * 4 descriptor ranges). Those filters should also indicate mechanistic aspects of the PPAR-δ agonists. The total number of appearances of descriptors in this table is 205 out of the 272. Considering that 186 descriptors could be randomly distributed among the 68 filters, each descriptor would appear between 1-2 times.

| Descriptor name | % in model (appearances) |
| --- | --- |
| a_count | 99 (67) |
| Q_VSA_PPOS | 32 (22) |
| Q_VSA_PNEG | 31 (21) |
| Q_VSA_FPOS | 24 (16) |
| a_Ni | 21 (14) |
| vsa_acc | 18 (12) |
| Q_VSA_FHYD | 12 (8) |
| BCUT_PEOE_2 | 10 (7) |
| KierA3 | 10 (7) |
| SMR_VSA7 | 10 (7) |
| opr_brigid | 9 (6) |
| PEOE_VSA-2 | 9 (6) |
| PEOE_VSA_POL | 9 (6) |
| TPSA | 9 (6) |

Figure 6A:
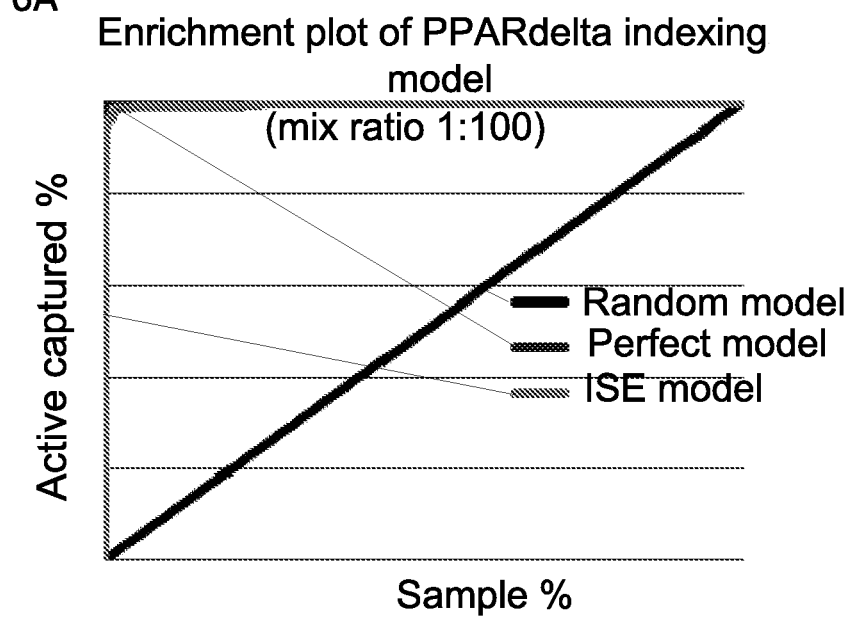
FIGS. 6A-B.
Figure 6B:
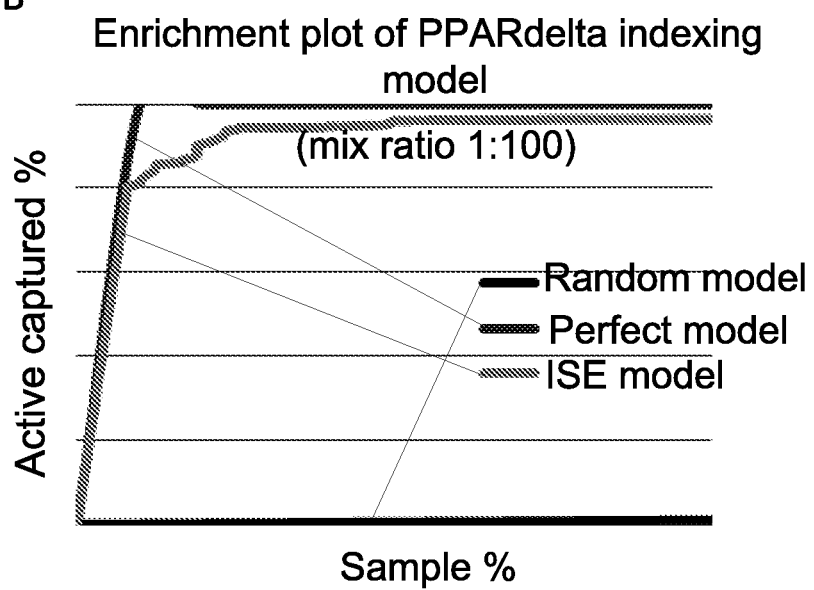

FIG. 6A-B shows Enrichment plot (FIG. 6A) and Enrichment plot of the highest indexed 1% of chemicals (FIG. 6B).

Figure 7A:
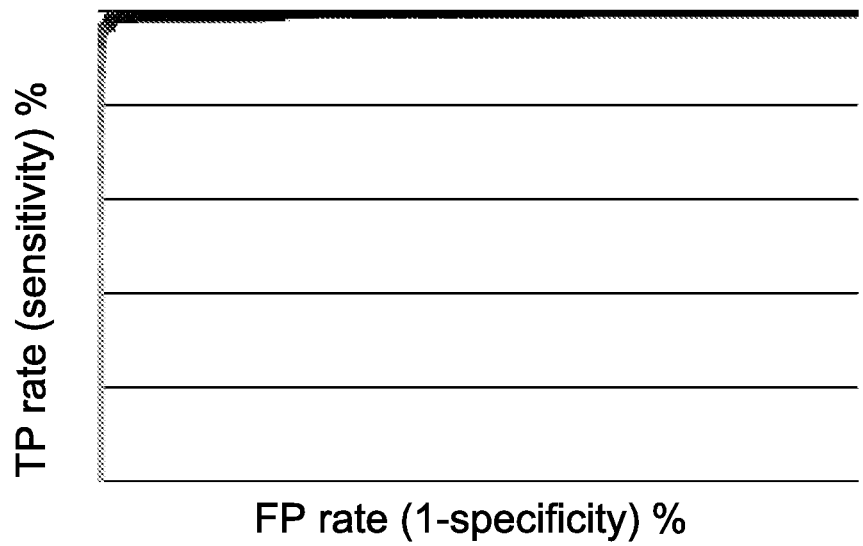
FIGS. 7A-B.
Figure 7B:
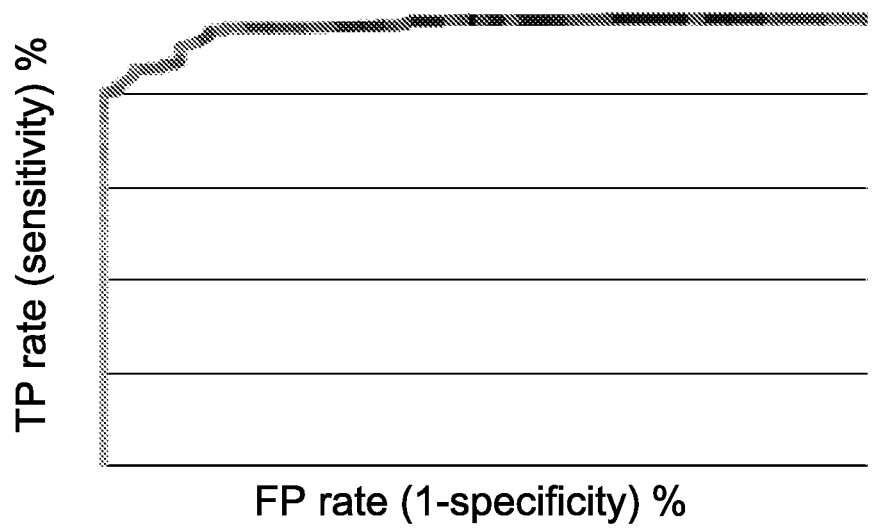

FIG. 7A-B depicts a receiver operating characteristic (ROC) curve (FIG. 7A) and the ROC curve of the highest indexed 1% chemicals (FIG. 7B). The area under the ROC curve is above 0.98, revealing highly accurate and efficient model.

TABLE 2

Numbers of ENAMINE molecules that achieved different scores by the ISE model.

| MBI Threshold | % True Positives | No. of commercial molecules over than | % of commercial molecules |
| --- | --- | --- | --- |
| −25 | 100 | 1563097 | 100 |
| −20 | 99 | 320041 | 20.47 |
| −15 | 99 | 170624 | 10.91 |
| −10 | 99 | 92395 | 5.91 |
| −5 | 99 | 42404 | 2.71 |
| 0 | 99 | 18604 | 1.19 |
| 5 | 96 | 8111 | 0.51 |
| 10 | 95 | 2491 | 0.16 |
| 15 | 87 | 711 | 0.04 |
| 20 | 75 | 129 | 0.008 |
| 25 | 36 | 0 | 0 |

TABLE 3

Geometrical data as well as energy score of the selected poses in the re-docking.

| The complex | Number of "crucial to H-bonds" residues with distance <3.5 Å to the selected pose | Number of "important" residues with distance <5 Å to the selected pose | Energy score (Fred) |
| --- | --- | --- | --- |
| 1GWX a | 10 | 3 | −123.12 |
| 1GWX b | 10 | 2 | −115.35 |
| 3GWX a | 10 | 3 | −77.00 |
| 3GWX b | 10 | 3 | −87.16 |
| 3D5F a | 10 | 3 | −100.93 |
| 3D5F b | 10 | 3 | −103.60 |
| 3GZ9 | 9 | 2 | −69.19 |

None of the poses in the case of 3ET2's re-dockings fulfilled the criteria.

TABLE 4

Ranges of Lipinski properties based on ~1200 known agonists of PPAR-δ*.

| Property | Average | Standard Deviation | Range |
| --- | --- | --- | --- |
| Hydrogen bond acceptors (lip_acc) | 5.71 | 1.31 | 3.08-8.33 |
| Hydrogen bond donors (lip_don) | 0.26 | 0.53 | 0-1.33 |
| LogP (o/w) | 6.13 | 1.33 | 3.47-8.80 |
| Molecular Weight | 477.24 | 59.32 | 359-596 |

The above ranges are "applicability domain": it is expected that in a "learning set" in which we mix known actives with "assumed inactives" we should pick the "decoys" (inactives) to be in the same "properties domain" as the actives. Thus, for this docking, 1000 molecules, which are within the applicability domain of the actives, were picked randomly from Enamine commercially available database.
*Values are averages +/−2 Standard deviations.

TABLE 5

$EC_{50}$ values of 64 molecules, which are not agonists for PPAR-δ, but the other PPARs.

| Name | $EC_{50}$ PPAR-δ (µM) | $EC_{50}$ PPAR-α (µM) | $EC_{50}$ PPAR-γ (µM) |
| --- | --- | --- | --- |
| T0519-9550 | 10.000 | >10 | 0.277 |
| T6970553 | 10.000 | 7.638 | 0.348 |
| T5981093 | 10.000 | 4.811 | 0.949 |
| T6009822 | 10.000 | >10 | 1.191 |
| T6752465 | 10.000 | 4.555 | 1.205 |
| T6121200 | 10.000 | 7.404 | 1.287 |
| T5367928 | 10.000 | 2.201 | 1.610 |
| T5486524 | 10.000 | 1.379 | 1.701 |
| T6004945 | 10.000 | 8.832 | 2.048 |
| T5592463 | 10.000 | >10 | 2.060 |
| T5628375 | 10.000 | >10 | 2.283 |
| T5501687 | 10.000 | 1.599 | 2.784 |
| T5284148 | 10.000 | >10 | 4.145 |
| T6986392 | 10.000 | 3.132 | 4.718 |
| T5483748 | 10.000 | 3.332 | 5.369 |
| T5492492 | 10.000 | 4.446 | 5.839 |
| T5807049 | 10.000 | >10 | 6.004 |
| T6291645 | 10.000 | >10 | 6.022 |
| T5335018 | 10.000 | >10 | 6.265 |
| T5330889 | 10.000 | >10 | 6.309 |
| T0519-8799 | 10.000 | >10 | 6.442 |
| T6000213 | 10.000 | >10 | 6.870 |
| T6754162 | 10.000 | >10 | 6.916 |
| T0511-1281 | 10.000 | >10 | 7.008 |
| T6773671 | 10.000 | 8.761 | 7.013 |
| T0519-8792 | 10.000 | >10 | 7.055 |
| T6610369 | 10.000 | >10 | 7.183 |
| T5569503 | 10.000 | >10 | 7.203 |
| T5349357 | 10.000 | >10 | 7.214 |
| T5389454 | 10.000 | >10 | 7.290 |
| T5470599 | 10.000 | 6.772 | 7.471 |
| T5373680 | 10.000 | 2.356 | 7.774 |
| T5662965 | 10.000 | >10 | 7.842 |
| T5375021 | 10.000 | >10 | 8.056 |
| T6272279 | 10.000 | >10 | 8.112 |
| T6711938 | 10.000 | >10 | 8.356 |
| T5287095 | 10.000 | >10 | 8.617 |
| T5234137 | 10.000 | >10 | 8.749 |
| T0518-4840 | 10.000 | 2.477 | 8.754 |
| T5932895 | 10.000 | >10 | 8.759 |
| T6623510 | 10.000 | >10 | 9.050 |
| T0516-9261 | 10.000 | 7.466 | 9.254 |
| T5292851 | 10.000 | >10 | 9.416 |
| T6875127 | 10.000 | 4.698 | 9.904 |
| T6025157 | 10.000 | 1.198 | >10 |
| T6720039 | 10.000 | 1.645 | >10 |
| T5424541 | 10.000 | 1.857 | >10 |
| T6018263 | 10.000 | 4.643 | >10 |
| T6192882 | 10.000 | 4.784 | >10 |
| T6046611 | 10.000 | 5.979 | >10 |
| T6785533 | 10.000 | 6.823 | >10 |
| T5936449 | 10.000 | 7.699 | >10 |

TABLE 5-continued

EC$_{50}$ values of 64 molecules, which are not agonists for PPAR-δ, but the other PPARs.

| Name | EC$_{50}$ PPAR-δ (μM) | EC$_{50}$ PPAR-α (μM) | EC$_{50}$ PPAR-γ (μM) |
| --- | --- | --- | --- |
| T5901519 | 10.000 | 7.754 | >10 |
| T5872814 | 10.000 | 7.852 | >10 |
| T5224095 | 10.000 | 8.204 | >10 |
| T6129595 | 10.000 | 8.311 | >10 |
| T5465128 | 10.000 | 8.320 | >10 |
| T6288701 | 10.000 | 8.374 | >10 |
| T6632619 | 10.000 | 8.829 | >10 |
| T5380005 | 10.000 | 8.881 | >10 |
| T0515-1394 | 10.000 | 8.911 | >10 |
| T6016677 | 10.000 | 9.017 | >10 |
| T5936399 | 10.000 | 9.551 | >10 |
| T5941878 | 10.000 | 9.939 | >10 |

TABLE 6

MBI for each of the molecules that were discovered by Wu et al [3].

| Agonist | EC$_{50}$ |
| --- | --- |
| Compound 1 | 13.80 |
| Compound 2 | 18.30 |
| Compound 3 | 17.58 |
| Compound 4 | 18.67 |
| Compound 5 | 17.62 |
| Compound 6 | 16.91 |
| Compound 7 | 13.10 |
| Compound 8 | 17.28 |
| Compound 9 | 17.62 |
| Compound 10 | 16.91 |
| Compound 11 | 17.95 |
| Compound 12 | 17.95 |
| Compound 13 | 18.67 |
| Compound 14 | 18.67 |
| Compound 15 | 17.58 |
| Compound 16 | 18.67 |

Figure 8A:
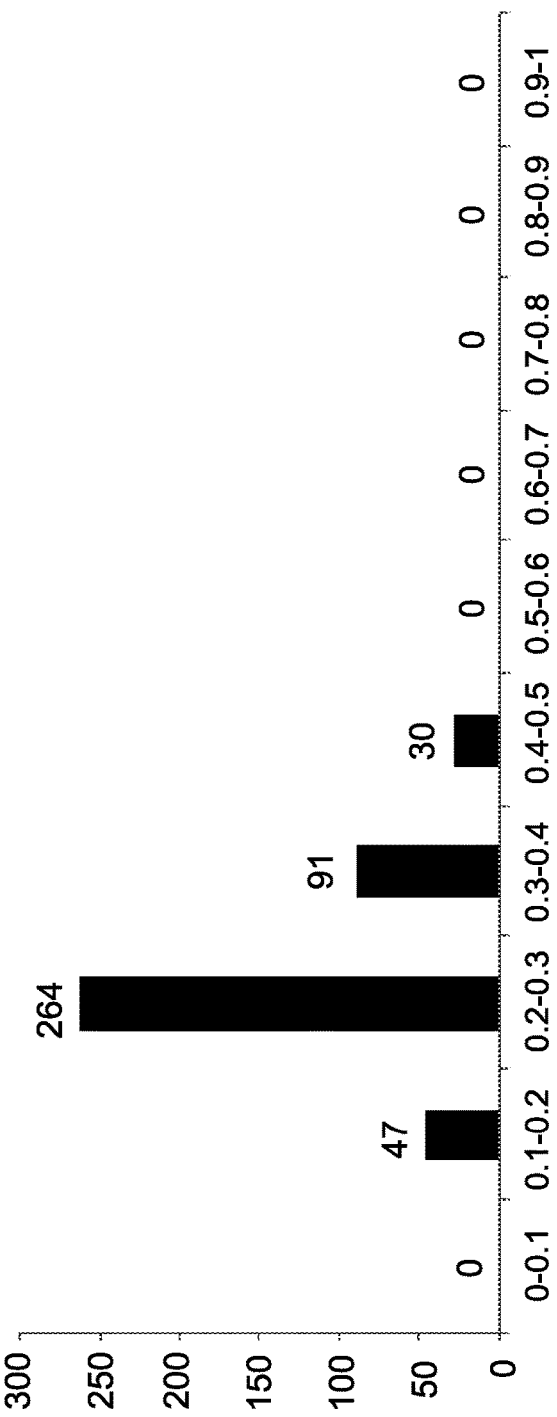
FIGS. 8A-B show the distribution of Tanimoto values for the novel agonists of Wu et al [3].
Figure 8B:
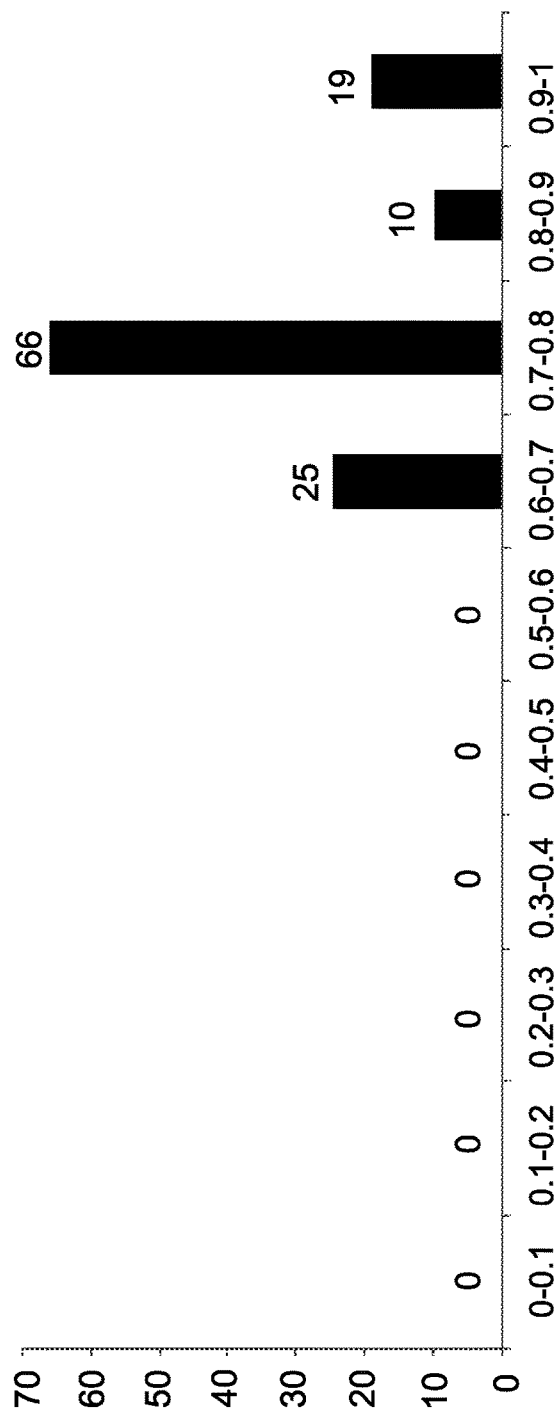

FIG. 8A-B shows distribution of Tanimoto values for the novel agonists of Wu et al [3]: FIG. 8A shows comparison vs. the novel agonists of the invention. FIG. 8B shows comparison of these novel agonists among themselves.

Results

PPAR-δ agonists dataset—agonist (789) were collected from different literature sources including CHEMBL and WOMBAT. The range of their agonist activities (EC$_{50}$) was 0.03-1000 nM. FIGS. 1-3 present some characteristics of those 789 PPAR-δ agonists. They partially obey Lipinski's Rule of Five (ROF) for Oral availability of drugs and Oprea's rules for "Lead like molecules" (63% and 25% of the ligands, respectively). The violations are mainly due to high lipophilicity and high molecular weight of PPAR-δ agonists. The range of molecular weights is between 300-600 Daltons. There are no hydrophilic ligands, and most are hydrophobic with c log P value above 3. However, their functional groups may potentially form strong specific interactions—hydrogen bonds and electrostatic interactions.

This dataset was divided in two, with one-half (394 molecules) serving as training set, and the others (395) as test set. Typically, active molecules are prone to be quite similar due to synthetic and other strategies applied for hit and lead optimization, often using the same scaffolds. To avoid such bias, the diversity of the training set of actives should be increased, by imposing a limit on similarity. On the other hand, a demand for high diversity might exclude too many molecules. FIG. 4 presents the numbers of active molecules that remain at each "cutting edge" of Tanimoto similarity in both the training and the test set. The 0.8 level presents a balance between having more diverse molecules and having enough molecules. Thus, 129 active molecules were excluded from the training set for model construction and 265 actives remained.

Five thousand molecules were collected randomly from the ENAMINE database to represent the set of "inactives"—the assumption is that, statistically, most of those randomly chosen molecules are inactive although they have not been confirmed. The set size of inactives is a compromise: it should represent accurately the properties' space of the inactives but the number should not be too large, which will extend computation time considerably (see discussion). Nearly 98% of these molecules have Tanimoto values of <0.4 to others. Those inactives were picked by limiting some of their properties based on the idea of an "applicability domain", as described in the SI methods. Applicability Domain is defined by the "chemical space" in which the training set should be developed for model construction. As the training set includes known actives and requires to be "diluted" with many inactives, those should be picked from the same "space". Some main properties should not bias the classification and therefore should not differ much from main properties of the "actives".

A model for identifying of PPAR-δ agonists was created by Iterative Stochastic Elimination (ISE) —a flowchart of the ISE process is presented in FIG. 5. The ISE modeling was performed with a training set of 5265 molecules, for classifying the 265 actives against the class of 5000 inactives. We generated sixty-eight unique filters, with four descriptors each, that distinguish best between PPAR-δ agonists and the inactive molecules. The top filter had MCC values of 0.97 (98% TP, 99% TN) and the least classifying filter that was kept had an MCC of 0.755 (91% TP, 84% TN). Filters have been clustered to ensure dissimilarity of >1% between filters. That is, if two filters are identical in the numbers of actives/inactives to the extent of >99%, the one with lower MCC is discarded. For details about the compositions of the filters—see Table 1.

The ISE model was validated by the test set—the test set contained 395 known agonists and 10,000 "newly picked" from ENAMINE. It was used in order to test the sixty-eight unique filters (the model). The model produced molecular bioactivity index (MBI) for each molecule in the test set. The MBI score is a result of the number of filters successfully passed (by having properties that adequately fit the 4 descriptor ranges of a filter), which add their TP/FP value to the successfully passed molecule, while missing any filter (if one non-fitting descriptor's value of any filter is found in a molecule) reduces the MBI score by TP/FP of that filter The model was highly efficient for scoring bioactivity on PPAR-δ. More than 96% of the actives were captured at the top 1% scored screened set. The area under the ROC is above 0.98, revealing a highly accurate and efficient model. See the enrichment plots in FIG. 6 and ROC curve plots in FIG. 7.

In Table 1, each column represents an index (MBI) border between molecules considered to be positives (which are with higher MBI values) and those considered to be negatives, which have lower MBI values. As we know which ones, on each side, are actives or are assumed inactives, it is easy to compute the six values of each column. It is clear that enrichments are much larger at higher MBI values, while the numbers of TP become smaller, and so does the number of TN. However, MCC values do not change linearly and are maximal around the MBI value of 6. As much as there is no dramatic difference from +6 to +10, we deal in the discussion with our decision to pick from screening only molecules with MBI of 10 and higher.

TABLE 7

MCC scores and Enrichment Factor for the MBI model.

|  | −3.0 | MBI + 3.0 | Border + 6.0 | +9.0 | +10.0 | +13.0 |
|---|---|---|---|---|---|---|
| TN | 6048 | 9682 | 9876 | 9969 | 9983 | 10000 |
| FN | 12 | 81 | 110 | 150 | 211 | 277 |
| TP | 383 | 314 | 285 | 245 | 184 | 118 |
| FP | 3952 | 318 | 124 | 31 | 17 | 0 |
| Enrichment* | 2.5 | 25 | 58 | 199 | 268 | — |
| MCC | 0.616 | 0.774 | 0.736 | 0.665 | 0.547 | 0.419 |

*Calculated based on the assumption that none of the ENAMINE DB chemicals is active on PPAR delta.
A threshold of MBI ≥ 10.0 was used to construct the first focused library.

The ENAMINE database of 1.56 million molecules was screened through the model—only 2,491 molecules achieved an MBI score >10. These molecules were used for the next step of docking and then for the selection for in vitro tests. Table 2 presents the number of commercial molecules in ENAMINE, which have indexes over various thresholds. None of the 2,491 molecules were examined previously for PPAR-δ binding. The top 2,491 commercial molecules that got indexes above+10 in the ISE model were subject to docking with OpenEye's FRED. About 300 top molecules were purchased for in vitro binding experiments.

Five PDB complexes were collected according to criteria, and used to define the most important residues for docking—those PPAR-δ complexes were collected from the PDB according to the following conditions: 1. solved by X-ray crystallography; 2. in complex with a ligand, with published $EC_{50}$; and 3. the resolution is <2.50 Å. Table 2 presents data about the complexes. The Ramachandran Plots of 3GZ9 and 3D5F do not have any outliers, while 3ET2, 3GWX, and 1GWX have 2, 5 and ten outliers, respectively.

We used the five complexes in order to construct a list of interactions of protein residues with the crystallized ligands. Nearly 30 residues in those complexes have one or more close connections to their ligands by distance criteria as follows: The maximum distance between Donor-and acceptor in Hydrogen bonds (D-A) is 3.3 Å. The maximum distance for VdW interactions is 3.9 Å. Cys285, Thr288, Thr289, His323, Leu330, Ile364, His449, Met453, Leu469, and Tyr473 interact with more than three different ligands or create H-bonds with one of them, and these residues were defined as "important". In addition, His323, His449 and Tyr473 consistently create a Hydrogen bond with all the ligands and so we define them as "crucial to H-bonds".

Two PDB complexes were found optimal for docking—the criteria for success in docking are at least one pose out of 30 with distance <3.5 Å to at least 2 of the "crucial to H-bonds" residues, and distance <5 Å to at least 7 of the "important" residues. If a ligand has a few successful poses (out of 30) —the pose with the lowest energy score was selected. If none of the poses of a candidate ligand fulfill the criteria—the ligand is rejected.

In re-docking, we test how well the original ligand of a complex is predicted by the docking protocol. Except for the case of 3ET2, all the other ligands fulfilled the criteria described above. Geometrical data, as well as energy score, for each selected pose in the re-docking, is presented in Table 3.

|Since we search for novel agonists, a crucial test of the ability of the docking algorithm and a specific crystal complex is that of distinguishing between two sets of molecules, the known agonists and the inactives. The measure for success of discrimination between the sets is MCC. One hundred thirty-five molecules were picked out of the 789 agonists (each of them has Tanimoto value <0.7 to the others) and were tested on each one of the complexes. The criteria for success in docking were the same as in the re-docking validation test. Two chains (3D5Fa and 3D5Fb) of the same crystal complex and one complex, 3GZ9 identified the largest numbers of true positives (more than 100 out of the 135). Therefore, we continued to test, with only those complexes, the docking of the 1000 random molecules. Only a small number of those were docked successfully (to produce FP). These random molecules were different from the set that was described above. The ranges of the applicability domain are described in Table 4. Data of true positives (TP, out of 135), false positives (FP, out of 1000) and MCC values are presented in Table 8. The data regarding resolutions and Ramachandran plots support these results, as these complexes have better resolution and Ramachandran plot.

TABLE 8

Details about the complexes from the PDB.

| PDB | 1GWX | 3GXW | 3D5F | 3ET2 | 3GZ9 |
|---|---|---|---|---|---|
| Num. of chains | Homodimer | Homodimer | Homodimer | Homodimer | Monomer |
| Resolution (Å) | 2.5 | 2.4 | 2.2 | 2.24 | 2.0 |
| $EC_{50}$ (μM) | 0.19 | 4 | 0.53 | 1.3 | 0.054 |
| Ramachandran plot | 10 Outliers | 5 Outliers | No Outliers | 2 Outliers | No Outliers |
| Re-docking | Successful | Successful | Successful | Failure | Successful |
| TP* | 84/97 | 83/54 | 116/109 | 94/84 | 112 |
| FP** | Not determined | Not determined | 179/130 | Not determined | 143 |
| MCC | — | — | 0.68/0.68 | — | 0.69 |

*The value of TP is the number of the known agonist (out of 135), which succeeded in the docking test. In the case of homodimers, the two chains were tested and the second number is the test with chain B.
*The value of FP is the number of the inactive (out of 1000), which succeeded in the docking test. In the cases in which the TP is <100, there is no point doing this test because the MCC will be low anyway.

The 2491 molecules with top MBI scores were screened by docking to the three selected chains—the best results were picked based on "voting": 335 ISE hits were successfully docked to all three PPAR-δ complexes, 349 were successful in only two chains, and 489 were successful in one only. The 335 hits that were successful in docking to all the three selected PPAR-δ complexes are highly diverse in comparison to the 394 agonists of the training set. Tanimoto index <0.3 is found for 318 molecules to all the others, while the rest 17 molecules have Tanimoto index <0.4. Among these 318 hits, 306 were available for purchasing and sent to Genomics Institute of the Novartis Research Foundation (GNF) for the in vitro experiments.

$EC_{50}$ values (for activation) of the 306 candidates were determined for each of the three PPARs—GW501516 was used as the positive control for PPAR-δ with an $EC_{50}$ value of 0.001 μM for PPAR-δ ($EC_{50}$ values of 0.704 and 0.839 μM for PPAR-α and PPAR-γ, respectively). GW7647 was used as the positive control for PPAR-α with $EC_{50}$ value of 0.003 μM for PPAR-α ($EC_{50}$ values of 0.974 and 0.85 μM for PPAR-δ and PPAR-γ, respectively). GW1929 was used as the positive control for PPAR-γ with $EC_{50}$ value of 0.013 μM for PPAR-γ ($EC_{50}$ values of 1 μM for PPAR-δ and PPAR-α).

The in vitro results were categorized into four main classes: 1) agonists of PPAR-δ with highest affinity ($EC_{50}$<1 μM), 2) agonists of PPAR-δ with low affinity ($EC_{50}$>1 μM), 3) non-agonists of PPAR-δ but agonists of other PPARs and 4) non-agonists of PPARs. The first class has 14 hits (Table 9 and List C). Only one of them is a "pan-agonist" hitting all three targets (GNF-8560), two of them are agonists of PPAR-δ and PPAR-α only (GNF-3632 & GNF-6952), and two of them are agonists of PPAR-δ and PPAR-γ only (GNF-5295 & GNF-0341). All the remaining 8 agonists are selective for PPAR-δ. The second class has 13 hits (Table 10 and List B). Four of them are selective to PPAR-δ. The third class has 64 hits (Table 5). Most of them have low affinities. Only 3 of them have $EC_{50}$<1 μM for PPAR-γ and the best (GNF-6635) has $EC_{50}$=0.277 μM and is not active on the other two targets. The other two (GNF-7017 & GNF-1165) have $EC_{50}$<1 μM for PPAR-γ, and $EC_{50}$>1 μM for PPAR-α.

TABLE 9

$EC_{50}$ values of the top 14 molecules with strongest affinities ($EC_{50}$ <1 μM) for PPAR-δ. $EC_{50}$ values for the other PPARs are presented. Molecular structures are shown in List C.

| Name | PPAR-δ $EC_{50}$ (μM) | PPAR-α $EC_{50}$ (μM) | PPAR-γ $EC_{50}$ (μM) |
| --- | --- | --- | --- |
| GW501516 | 0.001 | 0.704 | 0.839 |
| GW7647 | 0.974 | 0.003 | 0.85 |
| GW1929 | 1 | 1 | 0.013 |
| GNF-0242 | 0.004 | >10 | >10 |
| GNF-8065 | 0.006 | >10 | >10 |
| GNF-8501 | 0.006 | >10 | >10 |
| GNF-3632 | 0.007 | 5.477 | >10 |
| GNF-6878 | 0.008 | >10 | >10 |
| GNF-8560 | 0.011 | 1.406 | 3.525 |
| GNF-0341 | 0.011 | >10 | 1.258 |
| GNF-6029 | 0.012 | >10 | >10 |
| GNF-9820 | 0.012 | >10 | >10 |
| GNF-5295 | 0.013 | >10 | 7.279 |
| GNF-5891 | 0.017 | >10 | >10 |
| GNF-7486 | 0.018 | >10 | >10 |
| GNF-6952 | 0.019 | 7.559 | >10 |
| GNF-9448 | 0.883 | 7.061 | 0.937 |

TABLE 10

$EC_{50}$ values of 13 molecules with lower affinities ($EC_{50}$ >1 μM) for PPAR-δ. $EC_{50}$ values for the other PPARs are presented too. For molecular structures - see List B.

| Name | PPAR-δ $EC_{50}$ (μM) | PPAR-α $EC_{50}$ (μM) | PPAR-γ $EC_{50}$ (μM) |
| --- | --- | --- | --- |
| GW501516 | 0.001 | 0.704 | 0.839 |
| GW7647 | 0.974 | 0.003 | 0.85 |
| GW1929 | 1 | 1 | 0.013 |
| GNF-6928 | 3.698 | 6.904 | 3.784 |
| GNF-5758 | 4.327 | 6.930 | 9.732 |
| GNF-9594 | 4.598 | >10 | >10 |
| GNF-4516 | 6.815 | 2.327 | >10 |
| GNF-5154 | 7.045 | >10 | >10 |
| GNF-7176 | 7.239 | >10 | >10 |
| GNF-9057 | 7.488 | 4.633 | 8.595 |
| GNF-0248 | 7.555 | 7.036 | >10 |
| GNF-1051 | 7.757 | 7.331 | >10 |
| GNF-8208 | 7.858 | >10 | >10 |
| GNF-4909 | 8.239 | 0.825 | 1.834 |
| GNF-1676 | 8.387 | 6.195 | 1.287 |
| GNF-9969 | 9.481 | 6.937 | 1.010 |

List B presents structures and $EC_{50}$ values of novel agonist hits (EC50>1 μM) of PPAR-δ, discovered in this study.

The novel agonists that were found by ISE are highly diverse with respect to other agonists—one of the advantages of our methods is due to the representation of molecules as sets of Physico-chemical properties and not as structural fragments. This has been repeatedly shown to lead to the discovery of novel scaffolds in our projects. Tanimoto index was used in the training set to eliminate active molecules that are similar at a level of Tanimoto index ~0.8 and higher.

We compared the novel agonists to the training and the test set of actives. It is a matrix of Tanimoto values (each row is a known agonist while each column is a newly discovered agonist). The highest value in this matrix is 0.57, indicating that novel agonists are very different from the known 789 agonists from the ChEMBL and WOMBAT databases. Another interesting result is the diversity among the 27 newly discovered agonists. None of the values is greater than T=0.7. Out of 351 Tanimoto values, only eight are with T>0.4, again indicating vast diversity of the novel agonists.

Figure 9A:
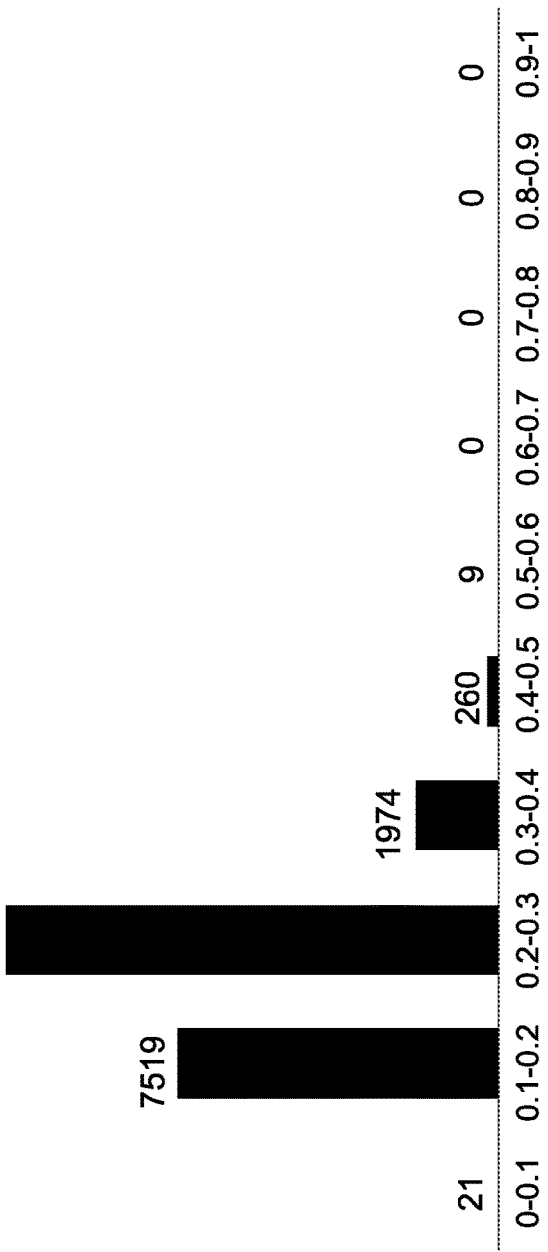
FIGS. 9A-C presents the distribution of Tanimoto values for the three comparisons.
Figure 9B:
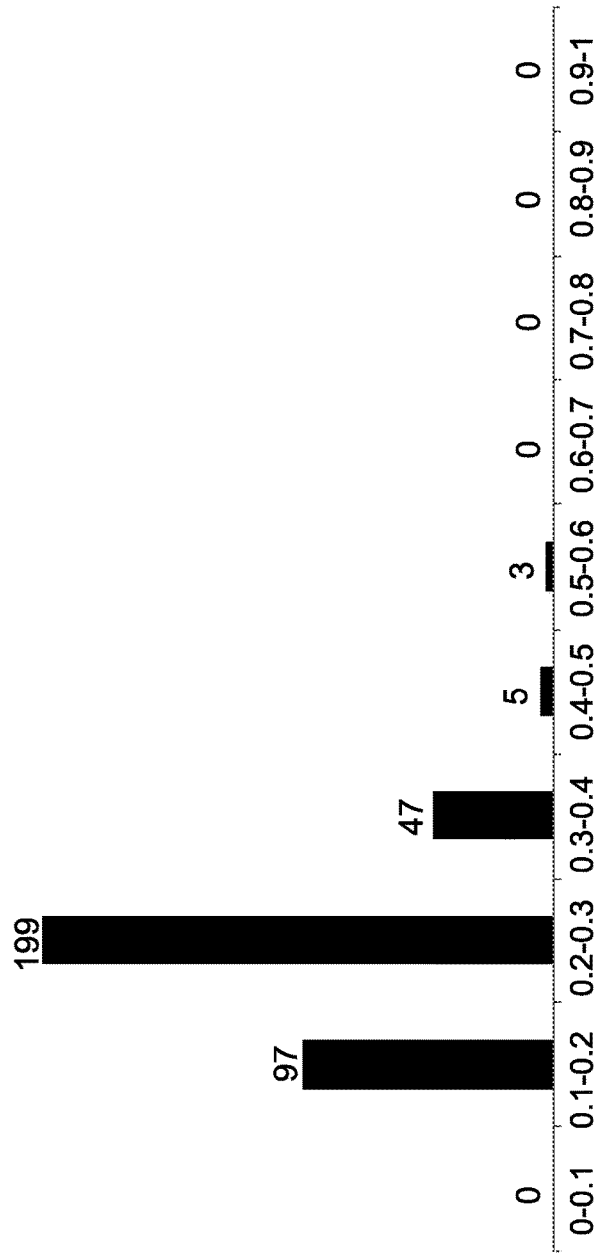
Figure 9C:
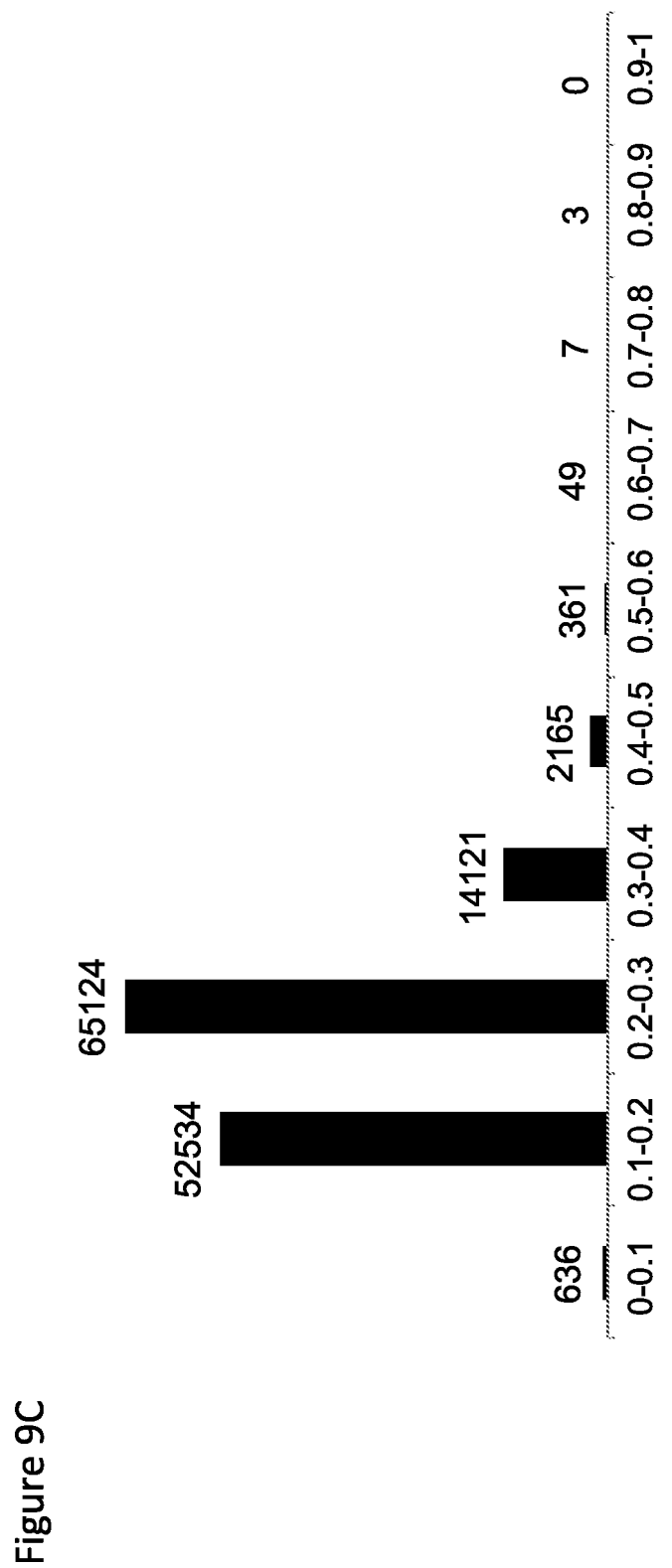

FIG. 9A-C presents the distribution of Tanimoto values for the three comparisons—the 789 known agonist set vs. novel agonists (FIG. 9A) and novel agonists among themselves (FIG. 9B). It is thus clear that all the new active scaffolds are diverse both concerning the "learning set" as well as with respect to each other. The third comparison is between the discovered 27 agonists and the randomly picked set of 5000. Only 10 out of the 135000 have T values above 0.7 (See FIG. 9C).

Recently, Wu et al [3] discovered 16 new agonists, all of which have high MBI scores of 13-19 in our models (Table 6), so the ISE model could identify them as agonists had they been in the dataset of the virtual screening. These agonists have no similarity to our novel agonists (see FIG. 8A). We searched for similar molecules of these agonists in the ENAMINE catalog (in order to check if our model missed potential agonists). Only four molecules out of the 1.56 million have similarities of Tanimoto value >0.7 to compound 1 (T0517-7230 & T5405641 have 0.74; T5681815 & T5999586 have 0.71). None of the ENAMINE molecules is similar to the other agonists.

Scaffolds of these new agonists are based on the substrate and are similar in most of the cases. FIG. 8B shows that all have Tanimoto values >0.6 to each other (and in most cases it is >0.7). Furthermore, 4 of these agonists (Compounds 1, 12, 13 & 14) have Tanimoto values >0.7 to the 789 known agonists (our training and test sets), while in the case of our novel agonists none has similarity to Tanimoto value >0.7 to the known agonists.

The invention claimed is:

1. A pharmaceutical composition comprising as an active ingredient a compound or a salt thereof and a pharmaceutically acceptable carrier, wherein the compound is a compound selected from the group consisting of:

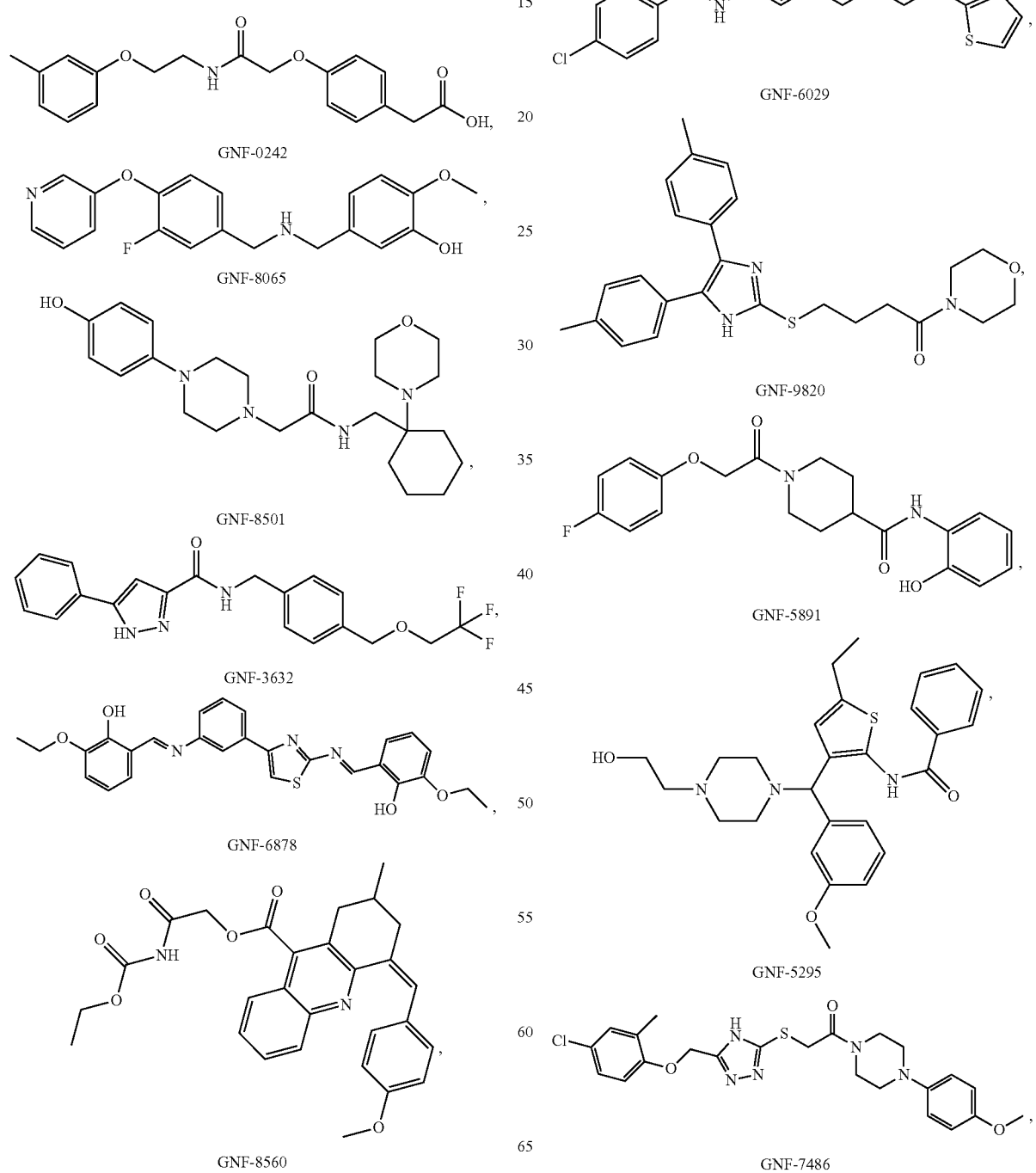

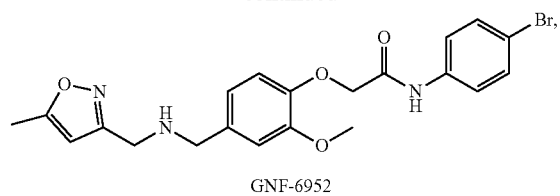
GNF-6952
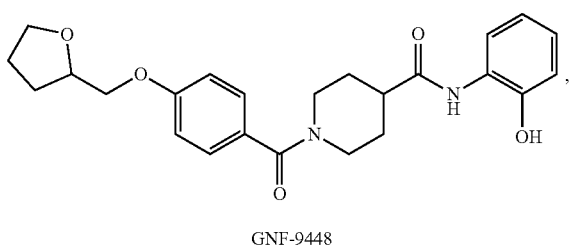
GNF-9448
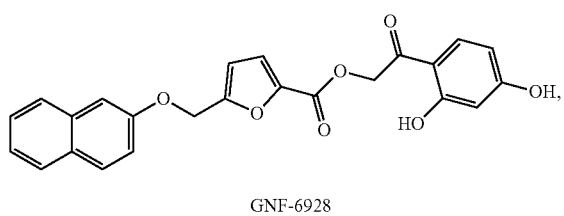
GNF-6928
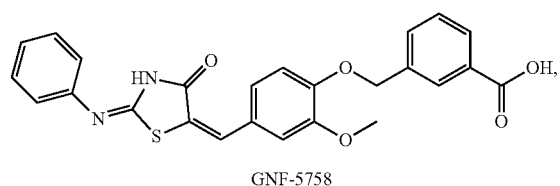
GNF-5758
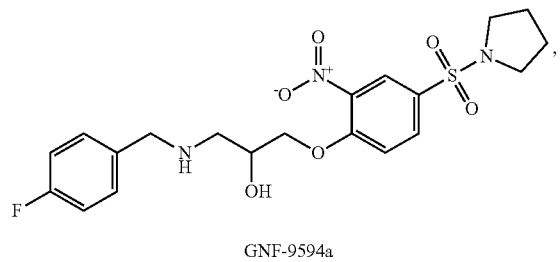
GNF-9594a
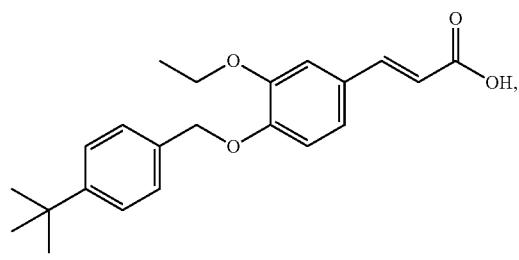
GNF-4516
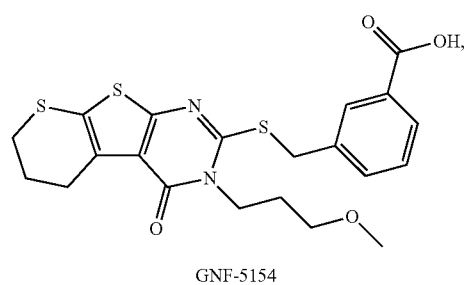
GNF-5154
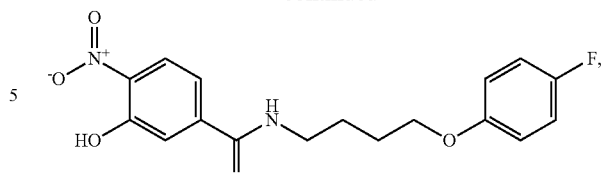
GNF-7176
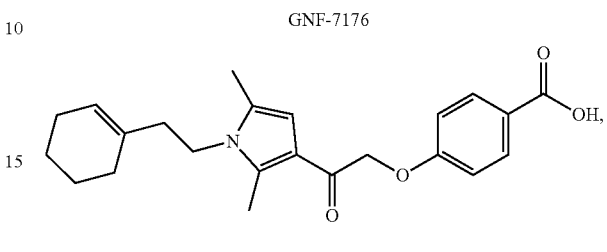
GNF-9057
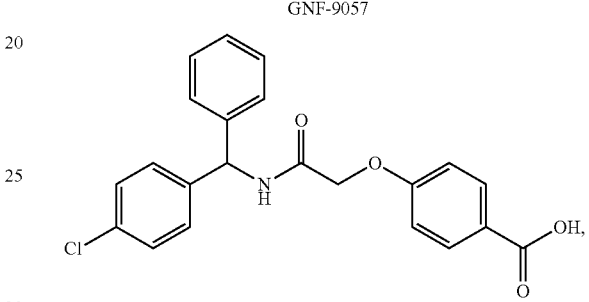
GNF-0248
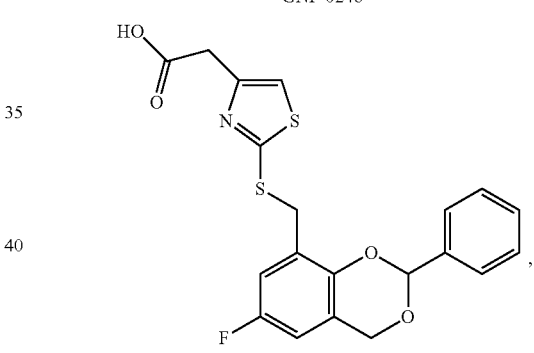
GNF-1051
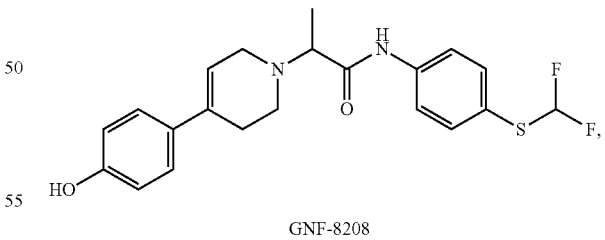
GNF-8208
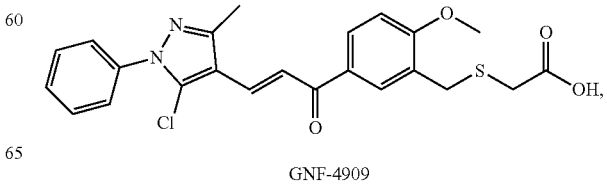
GNF-4909

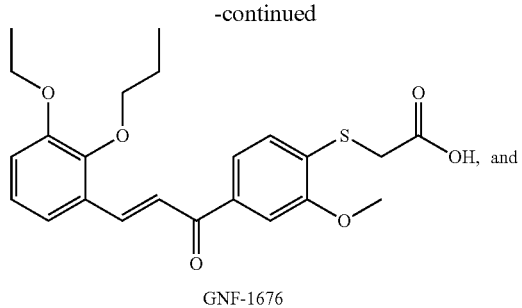
GNF-1676
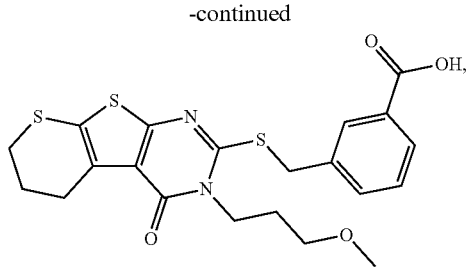
GNF-5154
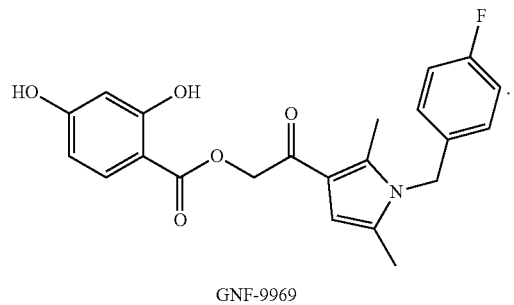
GNF-9969
2. The pharmaceutical composition according to claim 1, wherein the compound is selected from the group consisting of:
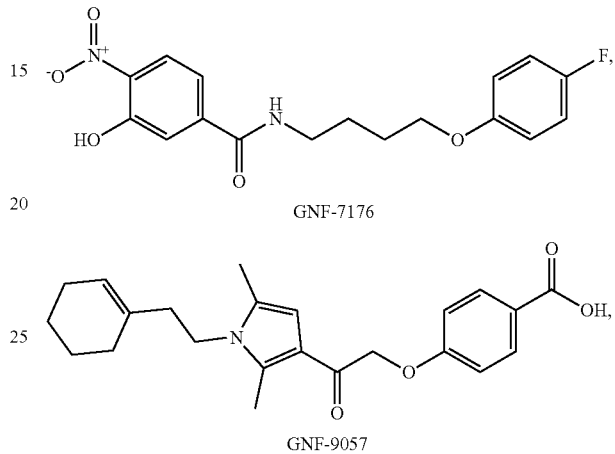
GNF-7176
GNF-9057
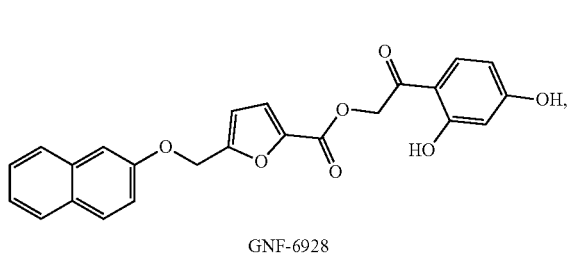
GNF-6928
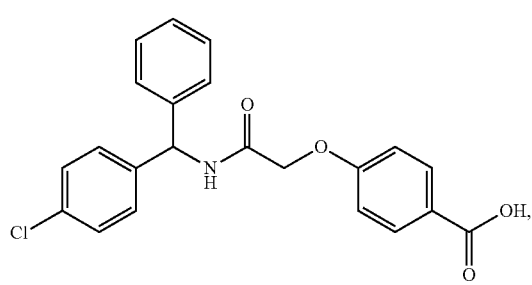
GNF-0248
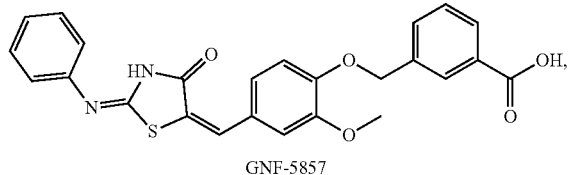
GNF-5857
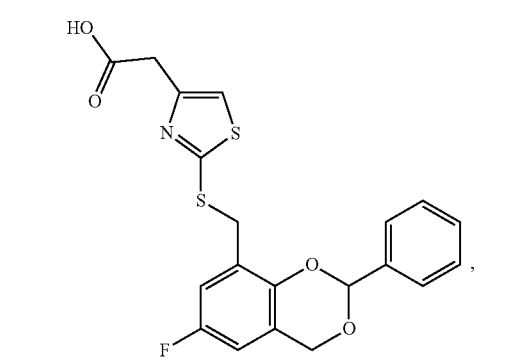
GNF-1051
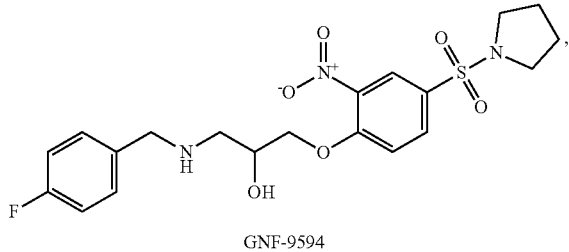
GNF-9594
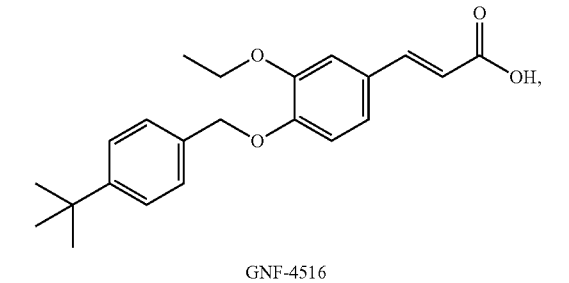
GNF-4516
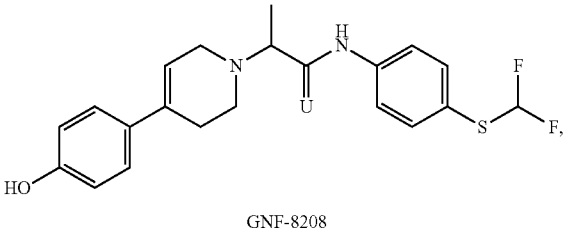
GNF-8208

-continued
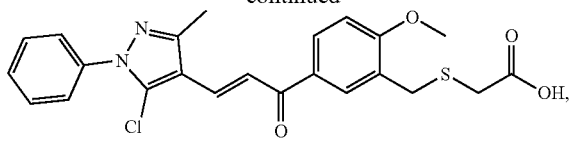
GNF-4909
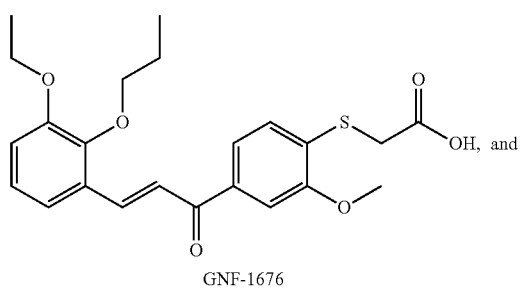
GNF-1676
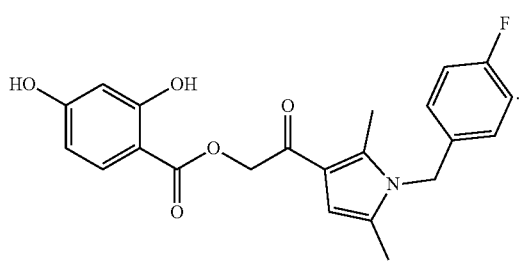
GNF-9969
3. The pharmaceutical composition according to claim 1, wherein the compound is selected from the group consisting of:
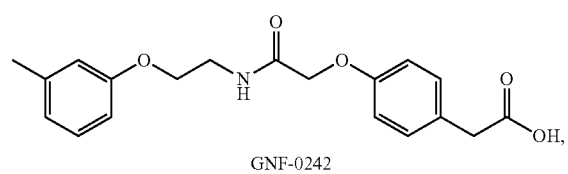
GNF-0242
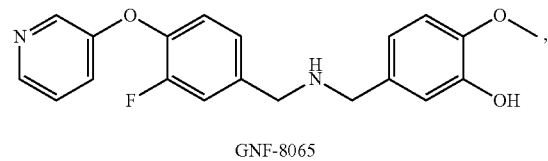
GNF-8065
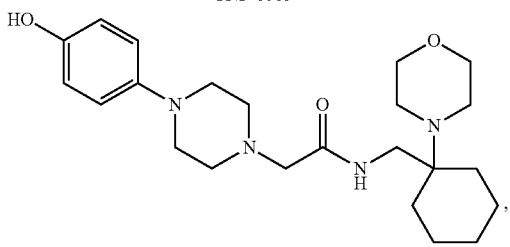
GNF-8501
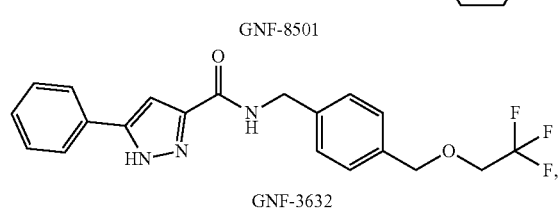
GNF-3632
-continued
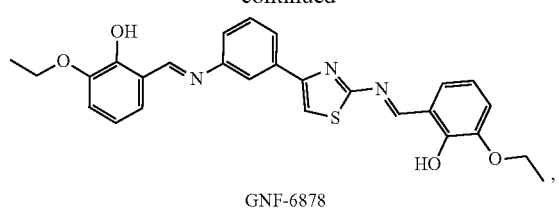
GNF-6878
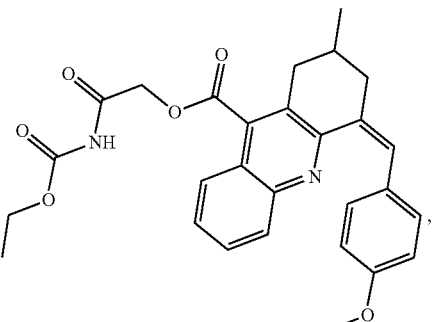
GNF-8560
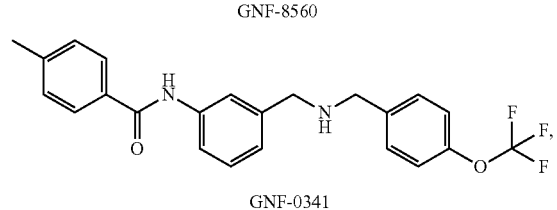
GNF-0341
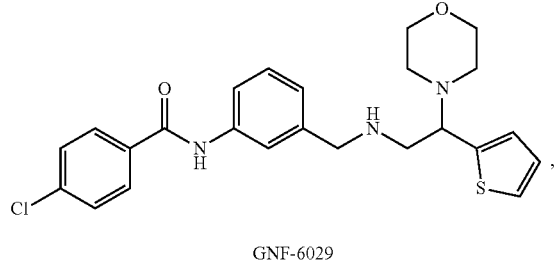
GNF-6029
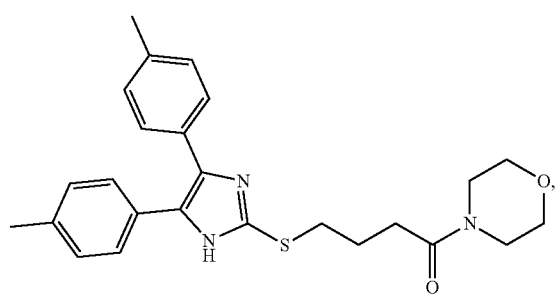
GNF-9820
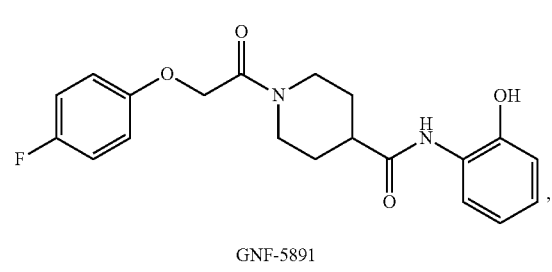
GNF-5891

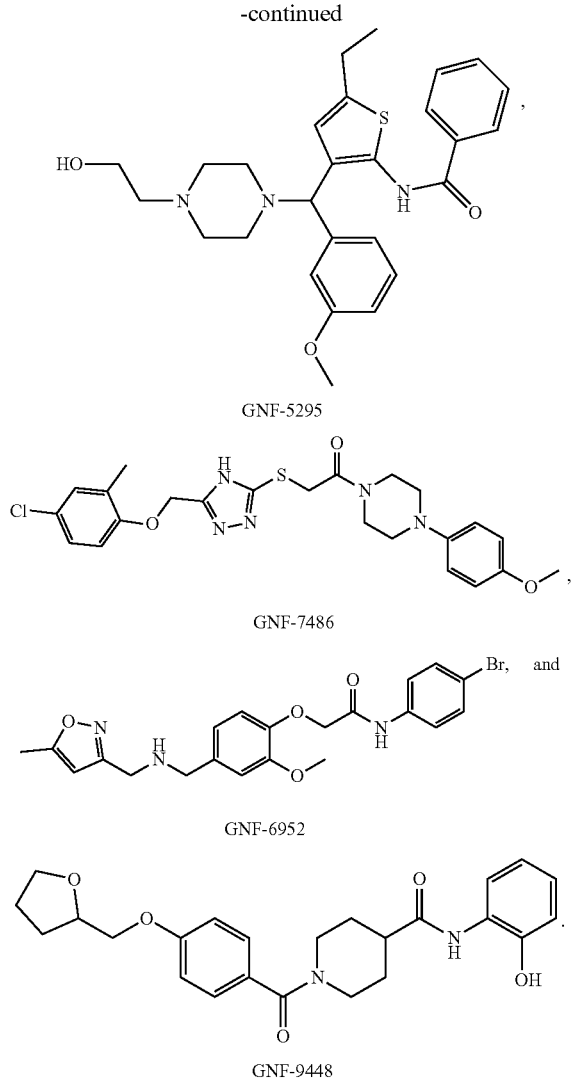
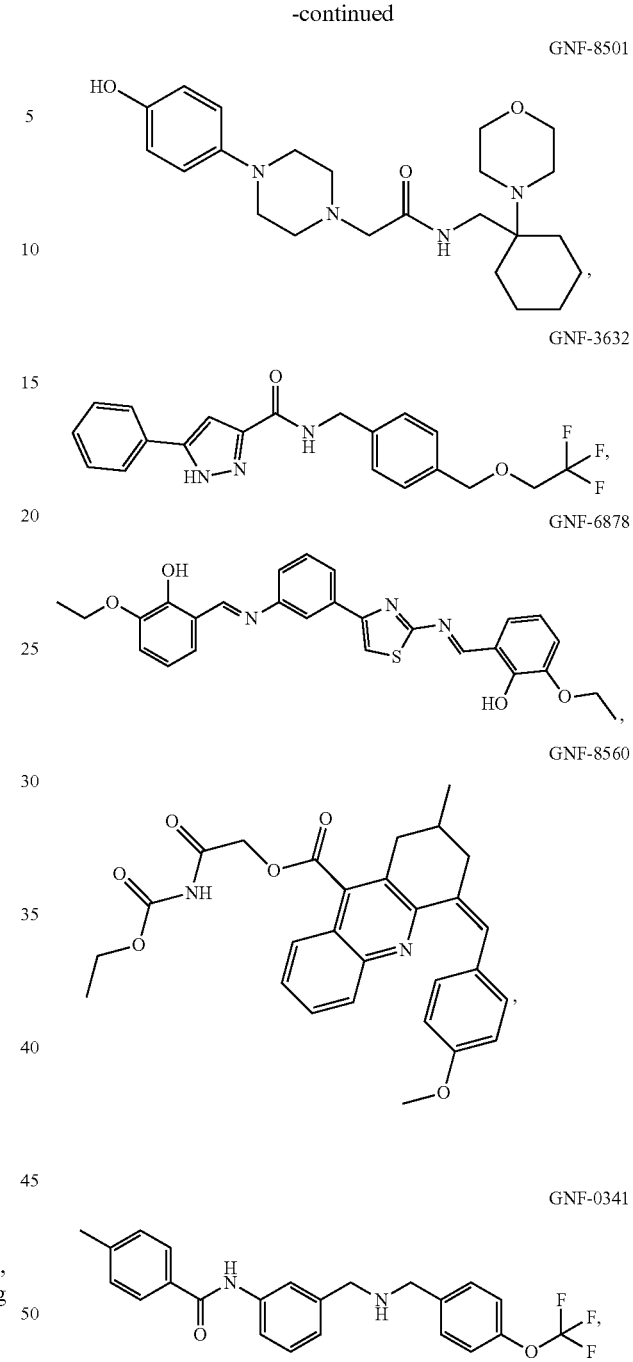
4. The pharmaceutical composition according to claim 1, wherein the compound is selected from the group consisting of:
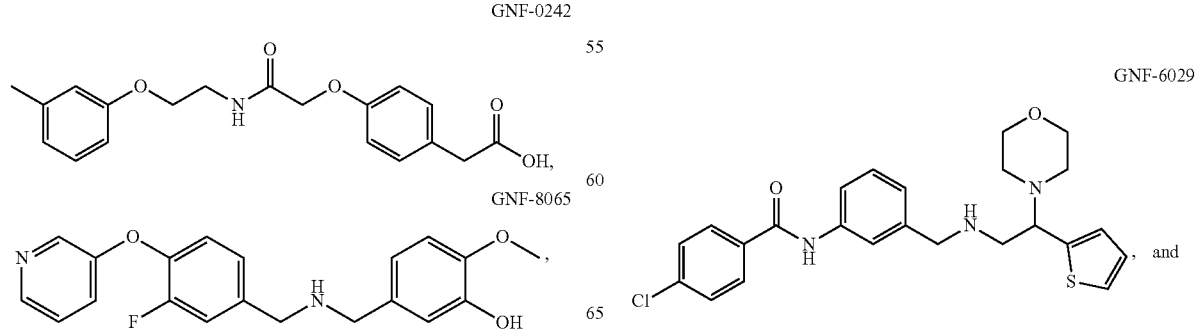

GNF-9820
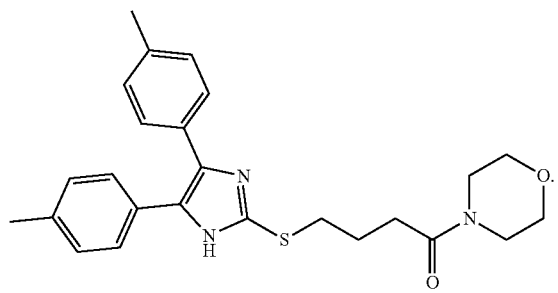
GNF-9448
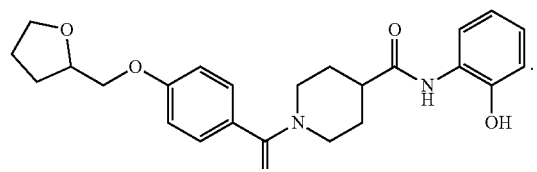
6. The pharmaceutical composition according to claim 1, wherein the compound is selected from the group consisting of:
5. The pharmaceutical composition according to claim 1, wherein the compound is selected from the group consisting of:
GNF-5891
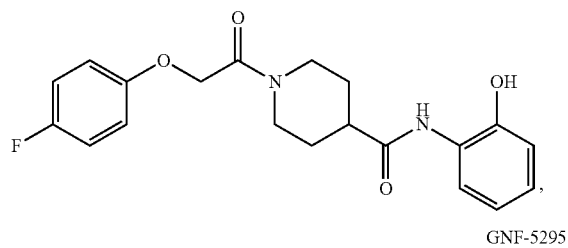
GNF-6928
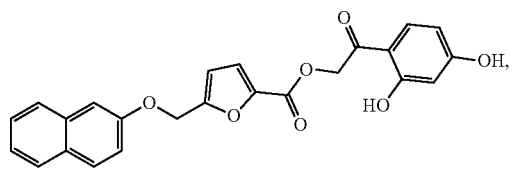
GNF-5295
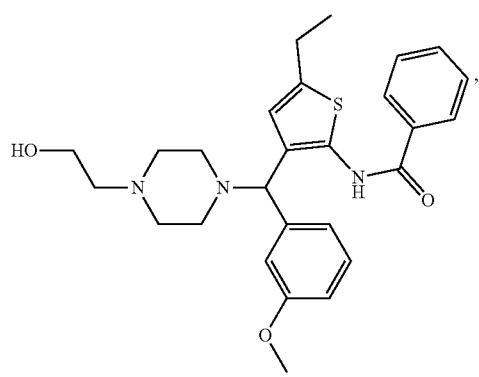
GNF-5758
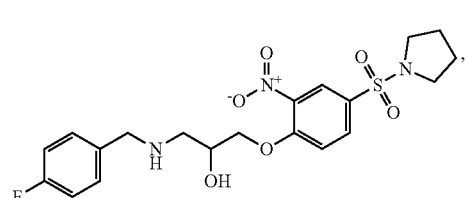
GNF-9594
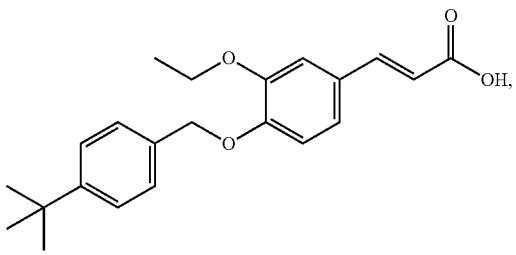
GNF-4516
GNF-7486
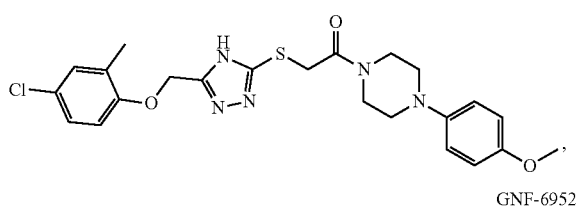
GNF-6952
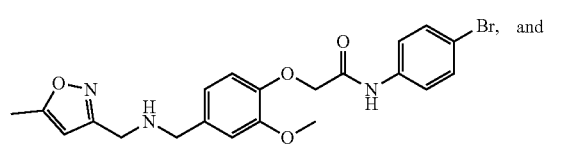
GNF-5154
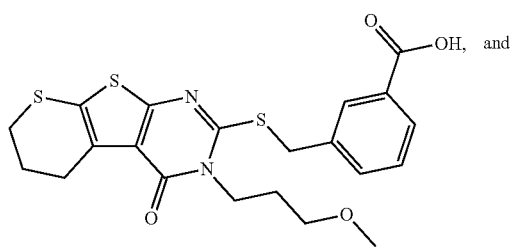, and -continued

GNF-7176

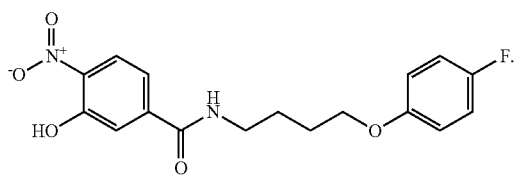

7. The pharmaceutical composition according to claim 1, wherein the compound is selected from the group consisting of:

GNF-9057

GNF-0248

GNF-1051

GNF-8208

GNF-4909

-continued

GNF-1676

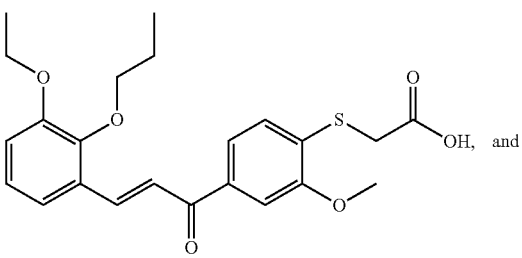

GNF-9969

8. The composition according to claim 1, wherein the composition is administered via oral administration, parenteral administration, sublingual administration, intranasal administration, transdermal delivery, intradermal delivery, subcutaneous delivery, intramuscular administration, intravenous administration, intrathecal administration, rectal administration, vaginal administration, intraocular administration, transdermal administration, or administration via the respiratory mucosal tissue.

9. The composition according to claim 1, wherein the composition is administered via pulmonary routes.

10. The pharmaceutical composition according to claim 1, for use in a method for modulating PPAR-δ activity comprising administering to a subject at least one compound selected from the group consisting of

GNF-0242

GNF-8065

GNF-8501

GNF-3632
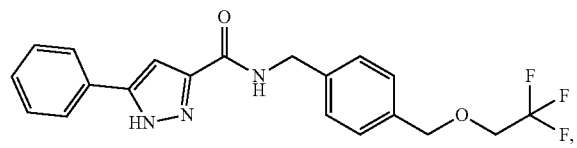
GNF-6878
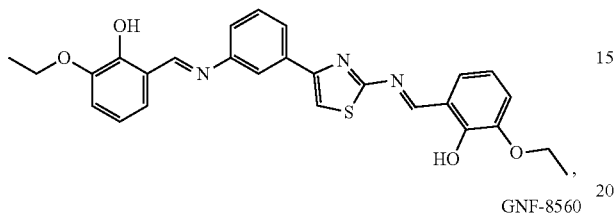
GNF-8560
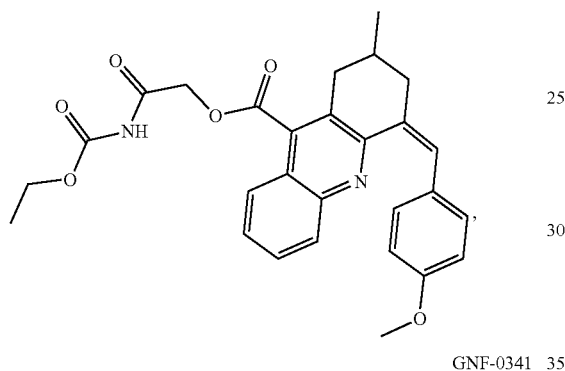
GNF-0341
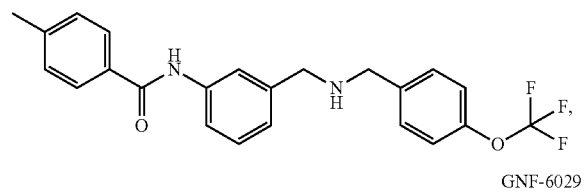
GNF-6029
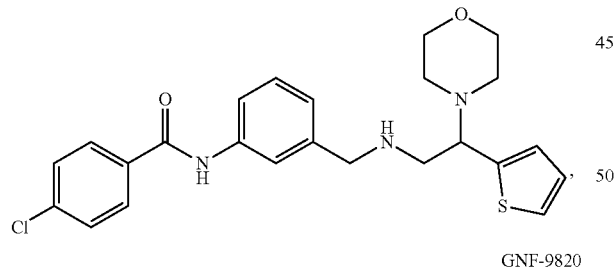
GNF-9820
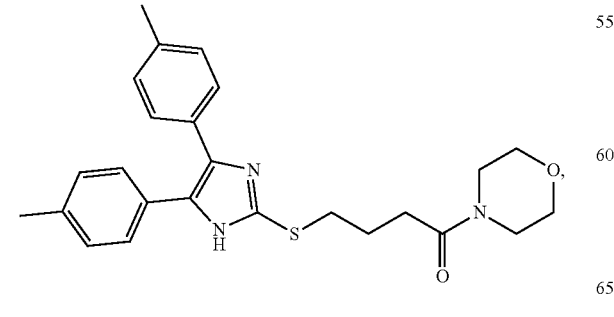
GNF-5891
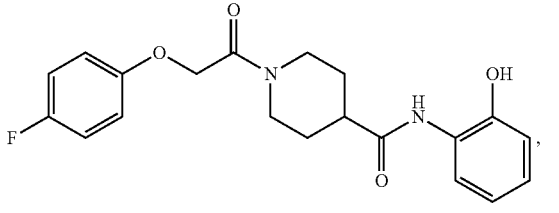
GNF-5295
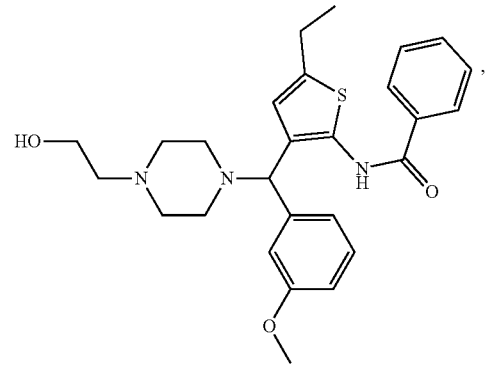
GNF-7486
GNF-6952
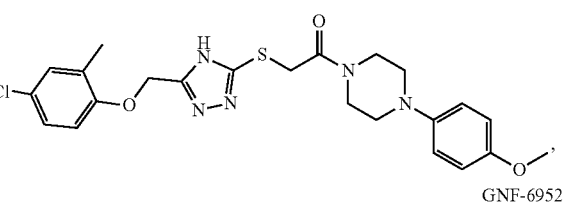
GNF-9448
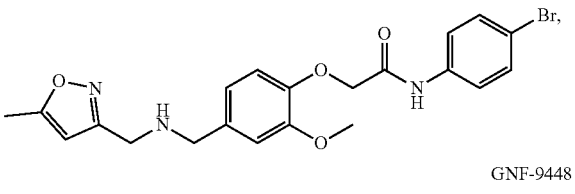
GNF-6928
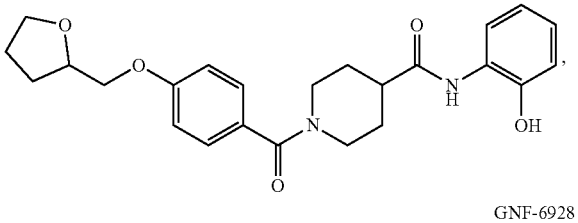
GNF-5758
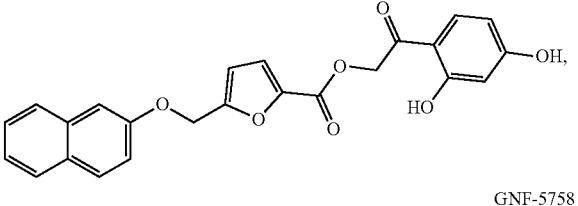
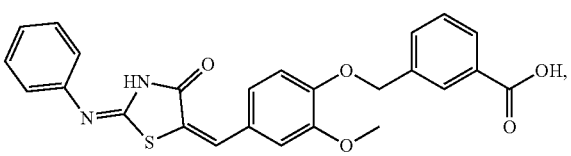

GNF-9594

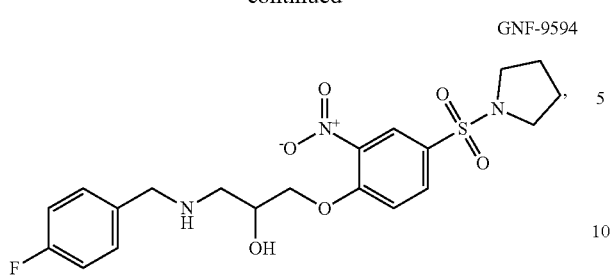

GNF-1051

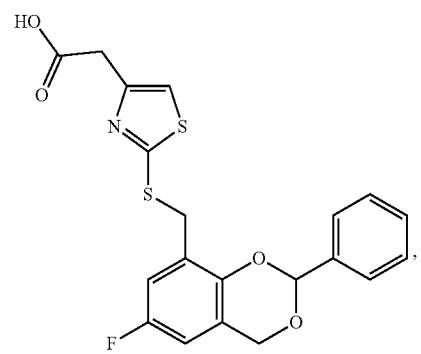

GNF-4516

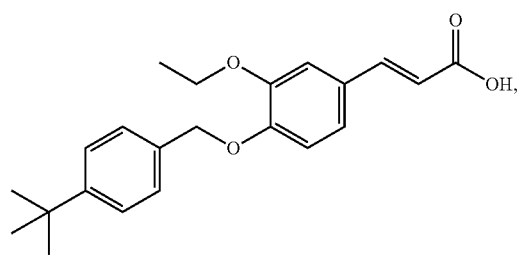

GNF-8208

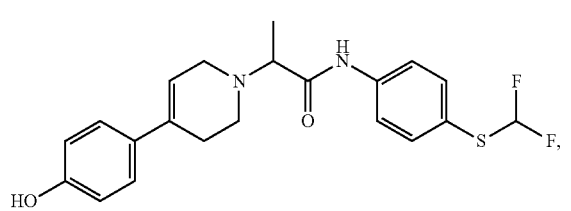

GNF-5154

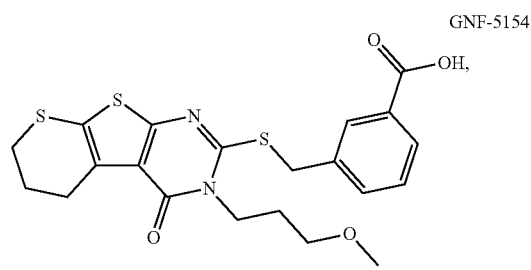

GNF-4909

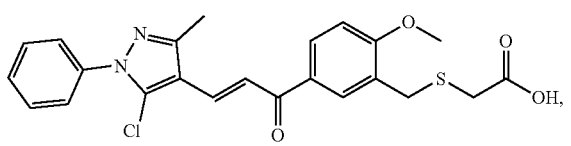

GNF-7176

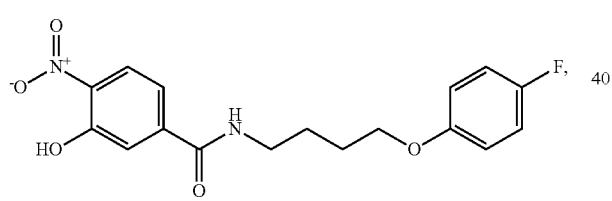

GNF-1676

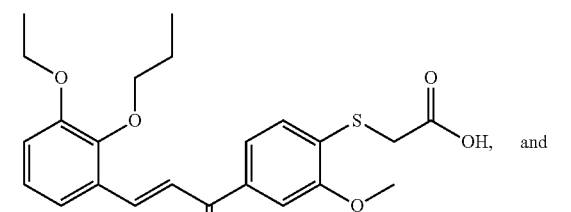

GNF-9057

GNF-9969

GNF-0248

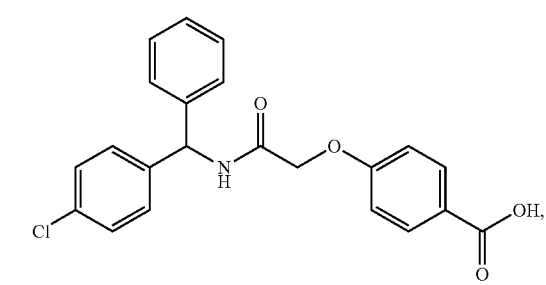

or a salt thereof.

11. The pharmaceutical composition according to claim 2, for use in a method for promoting exercise endurance comprising administering the composition to a subject.

12. A method for treating a disease or disorder in a subject, for modulating PPAR-δ activity the method comprising administering to the subject at least one composition according to claim 1.

13. The method according to claim 12, wherein the composition is administered via oral administration, parenteral administration, sublingual administration, intranasal administration, transdermal delivery, intradermal delivery, subcutaneous delivery, intramuscular administration, intravenous administration, intrathecal administration, rectal administration, vaginal administration, intraocular administration, transdermal administration, or administration via the respiratory mucosal tissue.

14. The method according to claim 12, wherein the composition is administered via pulmonary routes.

15. The method according to claim 12, wherein the method is for treating obesity, type 2 diabetes, increased serum low-density lipoprotein (LDL), increased serum triglycerides (TG), decreased serum high-density lipoprotein (HDL), cancer, atherosclerosis, atherogenic dyslipidemia, non-alcoholic fatty liver disease, epidermis disorders, inflammation after gut ischemia/reperfusion injury or lung inflammation.

16. A method for modulating PPAR-δ activity in vivo or in vitro, the method comprising contacting a cell or a tissue with at least one composition according to claim 1, wherein the cell or tissue is a cell or tissue of a subject or of a biological sample.

17. The method according to claim 12, wherein the composition comprises

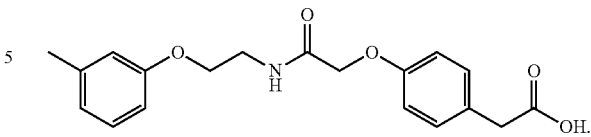

GNF-0242

18. A method for promoting exercise endurance in a subject, the method comprising administering to the subject the pharmaceutical composition of claim 1.

19. The method according to claim 18, wherein the composition comprises

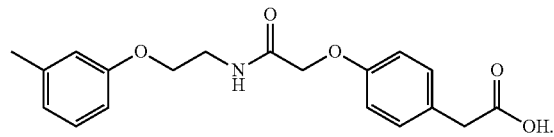

GNF-0242

* * * * *